US009834526B2

(12) United States Patent
McCauley et al.

(10) Patent No.: US 9,834,526 B2
(45) Date of Patent: Dec. 5, 2017

(54) HIV PROTEASE INHIBITORS

(71) Applicants: MERCK SHARP & DOHME CORP., Rahway, NJ (US); MERCK CANADA INC., Kirkland (CA)

(72) Inventors: John A. McCauley, Maple Glen, PA (US); Christian Beaulieu, Laval (CA); David Jonathan Bennett, Boston, MA (US); Christopher J. Bungard, Lansdale, PA (US); Sheldon Crane, Ile Perrot (CA); Thomas J. Greshock, Collegeville, PA (US); Katharine M. Holloway, Lansdale, PA (US); Daniel McKay, Ville St-Laurent, MA (US); Carmela Molinaro, Rahway, NJ (US); Oscar Miguel Moradei, Kirkland (CA); Satyanarayana Tummanapalli, Singapore Science Park III (SG); Vouy Linh Truong, Pierrefonds (CA); Peter D. Williams, Harleysville, PA (US)

(73) Assignees: MERCK SHARP & DOHME CORP., Rahway, NJ (US); MERCK CANADA INC., Kirkland, Quebec (CA)

( * ) Notice: Subject to any disclaimer, the term of this patent is extended or adjusted under 35 U.S.C. 154(b) by 0 days.

(21) Appl. No.: 15/104,510

(22) PCT Filed: Dec. 17, 2014

(86) PCT No.: PCT/US2014/070748
§ 371 (c)(1),
(2) Date: Jun. 14, 2016

(87) PCT Pub. No.: WO2015/095276
PCT Pub. Date: Jun. 25, 2015

(65) Prior Publication Data
US 2016/0311786 A1 Oct. 27, 2016

Related U.S. Application Data

(60) Provisional application No. 61/918,020, filed on Dec. 19, 2013.

(51) Int. Cl.
A61K 31/535 (2006.01)
C07D 265/28 (2006.01)
C07D 265/30 (2006.01)
A61K 45/06 (2006.01)
A61K 31/5375 (2006.01)
A61K 31/5377 (2006.01)
C07D 413/12 (2006.01)
C07D 413/14 (2006.01)
C07D 417/12 (2006.01)
C07D 417/14 (2006.01)
C07D 471/04 (2006.01)
C07D 487/04 (2006.01)
C07D 513/04 (2006.01)

(52) U.S. Cl.
CPC ........ *C07D 265/30* (2013.01); *A61K 31/5375* (2013.01); *A61K 31/5377* (2013.01); *A61K 45/06* (2013.01); *C07D 413/12* (2013.01); *C07D 413/14* (2013.01); *C07D 417/12* (2013.01); *C07D 417/14* (2013.01); *C07D 471/04* (2013.01); *C07D 487/04* (2013.01); *C07D 513/04* (2013.01)

(58) Field of Classification Search
CPC .......................... C07D 265/30; A61K 31/5377
USPC ...................... 544/98, 106; 514/238.8, 239.2
See application file for complete search history.

(56) References Cited

U.S. PATENT DOCUMENTS

| 5,196,438 A | 3/1993 | Martin et al. |
| 5,413,999 A | 5/1995 | Vacca et al. |
| 5,484,801 A | 1/1996 | Al-Razzak et al. |
| 5,484,926 A | 1/1996 | Dressman et al. |
| 5,585,263 A | 12/1996 | Hammarskj old et al. |
| 5,852,195 A | 12/1998 | Romines et al. |
| 8,497,383 B2 | 7/2013 | Coburn et al. |
| 9,315,475 B2 | 4/2016 | Beaulieu et al. |
| 2002/0077338 A1 | 6/2002 | Dressman et al. |
| 2003/0055071 A1 | 3/2003 | Anthony et al. |
| 2013/0158020 A1 | 6/2013 | Deng et al. |
| 2014/0018325 A1 | 1/2014 | Boyd et al. |
| 2014/0018326 A1 | 1/2014 | Moradei et al. |

(Continued)

FOREIGN PATENT DOCUMENTS

| WO | 0138332 A1 | 5/2001 |
| WO | 0230930 A2 | 4/2002 |
| WO | 2008157330 A1 | 12/2008 |

(Continued)

OTHER PUBLICATIONS

Daniel E. Patterson, et al, "Developement of a Practical Large-Scale Synthesis of Denagliptin Tosylate", Organic Process Research & Dev., 2009, pp. 900-906, vol. 13.
Hiroyuki Toh, et al, "Iose Structural Resemblance Between Putative Polymerase of a *Drosophila* Transposable Genetic Element 17.5 and Pol Gene Product of Moloney Murine Leukaemia Virus", The EMBO Journal, 1985, pp. 1267-1272, vol. 4, No. 5.
J.P. Vacca, et al, "L-735,524: An Orally Bioavailable Human Immunodeficiency Virus Type 1 Protease Inhibitor", Proc. Natl. Acad. Sci., Apr. 1994, pp. 4096-4100, vol. 91.

(Continued)

*Primary Examiner* — Shengjun Wang
(74) *Attorney, Agent, or Firm* — Carol S. Quagliato; Catherine D. Fitch

(57) ABSTRACT

The present invention is directed to 2,5,6-substituted morpholine derivatives and their use in the inhibition of HIV protease, the inhibition of HIV replication, the prophylaxis of infection by HIV, the treatment of infection by HIV, and the prophylaxis, treatment, and delay in the onset or progression of AIDS. The compounds and their salts can be employed as ingredients in pharmaceutical compositions, optionally in combination with other antivirals, immunomodulators, antibiotics or vaccines.

20 Claims, No Drawings

(56) References Cited

U.S. PATENT DOCUMENTS

2014/0303171 A1 10/2014 Boyd et al.

FOREIGN PATENT DOCUMENTS

| WO | 2009042093 | A1 | 4/2009 |
| WO | 2009042094 | A2 | 4/2009 |
| WO | 2012030685 | A2 | 3/2012 |
| WO | 2015017393 | A1 | 2/2015 |
| WO | 2015095265 | A1 | 6/2015 |
| WO | 2015134366 | A1 | 9/2015 |
| WO | 2015138220 | A1 | 12/2015 |

OTHER PUBLICATIONS

Joel R. Huff, "HIV Protease: A Novel Chemotherapeutic Target for AIDS", Journal of Medicinal Chemistry, 1991, pp. 2305-2314, vol. 34, No. 8, US.

Laurence H. Pearl, et al, "A Structural Model for the Retroviral Proteases", Nature, 1987, pp. 351-354, vol. 329.

Lee Ratner, et al, Complete Nucleotide Sequence of AIDS Virus, HTLV-III, Nature, 1985, pp. 277-284, vol. 313.

Michael D. Power, et al, "Nucleotide Sequence of SRV-1, a Type D Simian", Science, 1986, pp. 1567-1572, vol. 231.

Nancy E. Kohl., et al, "Active Human Immunodeficiency Virus Protease Is Required for Viral Infectivity", Proc. Natl. Acad. Sci., 1988, pp. 4686-4690, vol. 85.

Roy M. Gulick, et al, "Treatment With Indinavir, Zidovudine, and Lamivudine in Adults With Human Immunodeficiency Virus Infection and Prior Antiretroviral Therapy", New England Journal of Medicine, 1997, pp. 734-739, vol. 337.

Scott M. Hammer, et al, "A Controlled Trial of Two Nucleoside Analogues Plus Indinavir in Persons With Human Immunodeficiency Virus Infection and CD4 Cell Counts of 200 Per Cubic Millimeter or Less", The New England Journal of Medicine, 1997, pp. 725-733, vol. 337, No. 11.

HIV PROTEASE INHIBITORS

RELATED APPLICATIONS

This application is a 35 U.S.C. §371 filing from International Application No. PCT/US2014/070748, filed Dec. 17, 2014, which claims the benefit of U.S. Provisional Application No. 61/918,020, filed Dec. 19, 2013. Each of the aforementioned applications is herein incorporated by reference in its entirety.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus.

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Furthermore, the currently available protease inhibitors are rapidly metabolized and cleared from the bloodstream, requiring frequent dosing and use of a boosting agent. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

SUMMARY OF THE INVENTION

The present invention is directed to 2,5,6-substituted morpholine derivatives and their use in the inhibition of HIV protease, the inhibition of HIV replication, the prophylaxis of infection by HIV, the treatment of infection by HIV, and the prophylaxis, treatment, and delay in the onset or progression of AIDS.

DETAILED DESCRIPTION OF THE INVENTION

The invention encompasses a genus of compounds of Formula I:

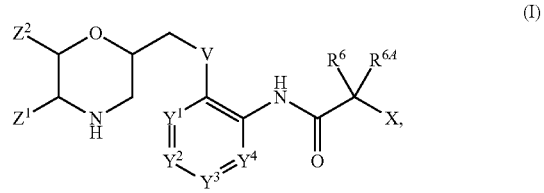

or a pharmaceutically acceptable salt thereof, wherein:

V is $CH_2$ or O;

$Y^1$, $Y^2$, $Y^3$ and $Y^4$ are independently selected from C(R) and N;

each X is independently selected from H and $NR^7R^8$;

$Z^1$ and $Z^2$ are independently selected from the group consisting of

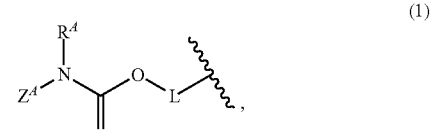

(1)

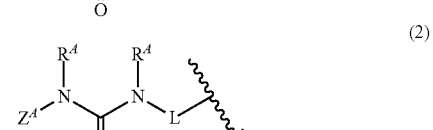

(2)

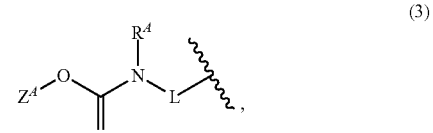

(3)

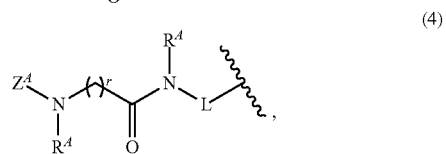

(4)

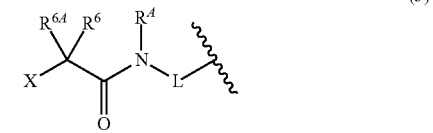

(5)

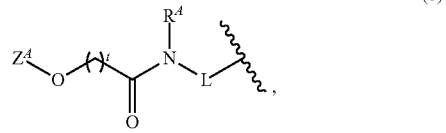

(6)

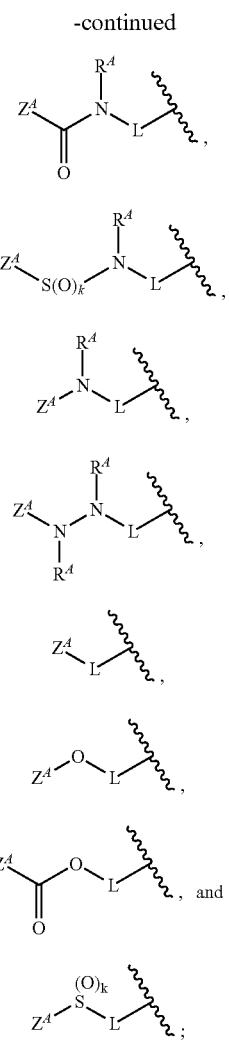

or $Z^1$ and $Z^2$ may be joined together with the atoms to which they are attached to form HetB;

L is a linker selected from
(a) a bond,
(b) —CH$_2$—,
(c) —C(O)—,
(d) —CH$_2$—C(O)— or —C(O)—CH$_2$—,
(e) —CH$_2$—CH$_2$—C(O)— or —C(O)—CH$_2$—CH$_2$—, and (f)

wherein ** shows the point of attachment to the morpholine;
R is selected from H, halo, hydroxy, C$_{1-4}$alkyl, C$_{1-4}$alkoxy, C$_{1-4}$alkyl-S(O)$_k$—, CF$_3$, CN, benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, C$_{1-4}$alkyl, C$_{1-4}$alkoxy, CF$_3$ and CN;

each k is independently 0, 1 or 2;
each r and t are independently 1, 2, 3 or 4;
$Z^A$ is selected from the group consisting of:
(1) hydrogen,
(2) C$_{1-10}$ alkyl,
(3) C$_{2-10}$alkenyl,
(4) C$_{3-7}$ cycloalkyl,
(5) AryA,
(6) HetA, and
(7) HetB, wherein said C$_{1-10}$ alkyl, C$_{2-10}$ alkenyl and C$_{3-7}$ cycloalky are optionally substituted with 1 to 6 substituents as allowed by valence independently selected from the group consisting of: fluoro, hydroxy, carbamoyl, C$_{3-6}$ cycloalkyl, C(O)O—C$_{1-6}$ alkyl, C(O)OH, C(O)—C$_{1-6}$ alkyl, N(H)—C$_{1-6}$ alkyl, N(—C$_{1-6}$ alkyl)$_2$, ArylA, HetA and HetB;

each $R^A$ is independently H or C$_{1-6}$ alkyl;

or $Z^A$ and $R^A$ and the nitrogen atom to which they are attached may be joined together to form a 5-, 6- or 7-membered mono-cyclic, or 9- or 10-membered bi-cyclic, saturated, aromatic or partially aromatic ring, said ring optionally containing 1 to 3 additional heteroatoms selected from O, S and N, and said ring optionally substituted with from 1 to 3 X$^A$;

$R^6$ is selected from:

wherein the asterisk (*) denotes the point of attachment to the rest of the compound and U$^1$ is selected from (1) H, (2)

$C_{1-10}$alkyl, wherein said $C_{1-10}$alkyl is optionally substituted with 1 to 4 substituents independently selected from halogen, $C_{1-4}$alkyl, $C_{1-4}$haloalkyl, hydroxy and $C_{1-4}$ alkoxy, (3) $C_{3-7}$ cycloalkyl, wherein said $C_{3-7}$ cycloalkyl is optionally substituted with 1 to 4 substituents independently selected from halogen, $C_{1-4}$alkyl, $C_{1-4}$haloalkyl, hydroxy and $C_{1-4}$alkoxy, (4) ArylA, (5) HetA, (6) HetB, (7) $C_{1-10}$alkyl substituted with ArylA, (8) $C_{1-10}$alkyl substituted with HetA, and (9) $C_{1-10}$alkyl substituted with HetB; and Ring B is selected from $C_{3-7}$ cycloalky and HetB, wherein $C_{3-7}$ cycloalkyl is optionally substituted with 1 to 4 substituents independently selected from halogen, OH, $C_{1-4}$alkyl, $C_{1-4}$fluorolkyl and $C_{1-4}$alkoxy;

each $R^{6A}$ independently is H or $C_{1-6}$ alkyl;

alternatively, $R^6$ and $R^{6A}$ together with the carbon to which they are attached form a $C_{3-6}$ cycloalkyl which is optionally substituted with phenyl, wherein the phenyl is optionally substituted with from 1 to 3 $X^D$;

each $X^A$, each $X^B$, each $X^C$, each $X^D$, each $Y^B$ and each $Y^C$ are independently selected from the group consisting of:
  (1) $C_{1-6}$ alkyl,
  (2) $C_{3-6}$ cycloalkyl,
  (3) $C_{1-6}$ haloalkyl,
  (4) OH,
  (5) O—$C_{1-6}$ alkyl,
  (6) O—$C_{1-6}$ haloalkyl,
  (7) O—$C_{3-6}$ cycloalkyl,
  (8) SH,
  (9) S—$C_{1-6}$ alkyl,
  (10) S—$C_{1-6}$ haloalkyl,
  (11) S—$C_{3-6}$ cycloalkyl,
  (12) halo,
  (13) CN,
  (14) $NO_2$,
  (15) $NH_2$,
  (16) N(H)—$C_{1-6}$ alkyl,
  (17) N(—$C_{1-6}$ alkyl)$_2$,
  (18) N(H)C(O)—$C_{1-6}$ alkyl,
  (19) N(H)CH(O),
  (20) CH(O),
  (21) C(O)—$C_{1-6}$ alkyl,
  (22) C(O)OH,
  (23) C(O)O—$C_{1-6}$ alkyl,
  (24) C(O)$NH_2$,
  (25) C(O)N(H)—$C_{1-6}$ alkyl,
  (26) C(O)N(—$C_{1-6}$ alkyl)$_2$,
  (27) C(O)N(H)C(O)—$C_{1-6}$ alkyl,
  (28) C(O)N(H)CH(O)
  (29) $SO_2$H,
  (30) $SO_2$—$C_{1-6}$ alkyl;
  (31) phenyl, benzyl or phenoxy, each optionally substituted with 1 to 5 substituents selected from halogen and $C_{1-6}$ alkyl,
  (32) HetA, —O-HetA or —$CH_2$—HetA, optionally substituted with 1 to 5 substituents selected from halogen and $C_{1-6}$ alkyl,
  (33) trimethylsilyl, and
  (34) $C_{2-6}$alkenyl,
  wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
    (a) $C_{1-6}$ haloalkyl,
    (b) OH
    (c) O—$C_{1-6}$ alkyl,
    (d) O—$C_{1-6}$ haloalkyl,
    (e) O—$C_{3-6}$ cycloalkyl,
    (f) SH,
    (g) S—$C_{1-6}$ alkyl,
    (h) halo,
    (i) CN,
    (j) $NO_2$,
    (k) $NH_2$,
    (l) N(H)—$C_{1-6}$ alkyl,
    (m) N(—$C_{1-6}$ alkyl)$_2$,
    (n) C(O)—$C_{1-6}$ alkyl,
    (o) C(O)OH,
    (p) C(O)O—$C_{1-6}$ alkyl, and
    (q) $SO_2$—$C_{1-6}$ alkyl;

T is O, S, S(O), or $SO_2$;

m is an integer equal to 0, 1, 2, or 3;

n is an integer equal to 0, 1, 2, or 3;

$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or $SO_2$—$R^K$;

$R^8$ is H, $C_{1-6}$ alkyl, $C_{1-6}$ haloalkyl or $C_{3-6}$ cycloalkyl;

$R^K$ is:
  (1) $C_{1-6}$ alkyl,
  (2) $C_{3-6}$ cycloalkyl,
  (3) $C_{1-6}$ alkyl substituted with $C_{3-6}$ cycloalkyl,
  (4) O—$C_{1-6}$ alkyl,
  (5) O—$C_{1-6}$ alkyl substituted with O—$C_{1-6}$ alkyl,
  (6) O—$C_{1-6}$ fluoroalkyl,
  (7) C(O)O—$C_{1-6}$ alkyl,
  (8) $C_{1-6}$ alkyl substituted with C(O)O—$C_{1-6}$ alkyl,
  (9) $C_{1-6}$ alkyl substituted with C(O)OH,
  (10) $C_{1-6}$ alkyl substituted with C(O)—$C_{1-6}$ alkyl,
  (11) N(H)—$C_{1-6}$ alkyl,
  (12) N(—$C_{1-6}$ alkyl)$_2$,
  (13) $C_{1-6}$ alkyl substituted with $NH_2$, N(H)—$C_{1-6}$ alkyl, or N(—$C_{1-6}$ alkyl)$_2$,
  (14) AryA,
  (15) $C_{1-6}$ alkyl substituted with AryA,
  (16) O—$C_{1-6}$ alkyl substituted with AryA,
  (17) HetA,
  (18) $C_{1-6}$ alkyl substituted with HetA,
  (19) O—$C_{1-6}$ alkyl substituted with HetA,
  (20) HetB,
  (21) O-HetB, or
  (22) O—$C_{1-6}$ alkyl substituted with HetB;

each AryA is an aryl which is independently phenyl or naphthyl, wherein the phenyl or naphthyl is optionally substituted with from 1 to 3 $Y^B$;

each HetA is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocylic ring (i) or the bicyclic ring (ii) is optionally substituted with from 1 to 3 $Y^C$; and each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with from 1 to 3 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)$NH_2$, C(O)N(H)—$C_{1-6}$ alkyl, C(O)N(—$C_{1-6}$ alkyl)$_2$, C(O)H, C(O)—$C_{1-6}$ alkyl, $CO_2$H, $CO_2$—$C_{1-6}$ alkyl, $SO_2$H, or $SO_2$—$C_{1-6}$ alkyl.

Another embodiment of the invention encompasses compounds of Formula I as described in the genus above, wherein each $X^A$, each $X^B$, each $X^C$, each $X^D$, each $Y^B$ and each $Y^C$ are selected from the substituents (1) to (34) as described in the genus, except that $C_{1-6}$ alkyl in each instance of (1), (3) (5), (6), (9), (10), (16), (17), (18), (21), (23), (25), (26), (27), (30), (31) and (32) is unsubstituted.

Within the genus, the invention encompasses a first sub-genus of compounds of Formula I wherein $R^6$ is:

[chemical structure]

wherein $W^1$ to $W^5$ are independently CH or N, with the proviso that no more that three are N, and $R^{6A}$ is H, and all other variables are as provided in the genus. $X^B$ and $X^C$ may be substituted on any substitutable position including, for $X^C$, $W^1$ to $W^5$ when any of the aforementioned are CH.

The invention also encompasses a second sub-genus of compounds of Formula I wherein $Z^1$ is $C_{1-6}$alkyl and $Z^2$ is

[chemical structures]

and L is —CH$_2$—, and all other variables are as provided in the genus or first sub-genus. In an embodiment within the second sub-genus, k is 0 and $Z^A$ is selected from phenyl, quinolinyl, oxadiazolyl, pyridinyl, quinoxaolinyl, pyrazolopyrimidinyl, thiadiazolyl, thiazolyl, oxazolyl, benzimidazolyl, pyrimidinyl, thiazololopyridinyl, imidazolopyridinyl, triazolyl and tetrazolyl, wherein said $Z^A$ is optionally substituted with 1 to 3 substituents independently selected from F, Cl, Br, methyl, cyano, trifluoromethyl, difluoromethoxy and amino.

Within the second sub-genus the invention encompasses a first class of compounds of Formula I wherein $Z^1$ is methyl, and all other variables are as provided in the second sub-genus.

The invention encompasses a third sub-genus of compounds of Formula I wherein $Z^1$ is

[chemical structures]

and $Z^2$ is

[chemical structures]

wherein L is —CH$_2$—, and all other variables are as provided in the genus or first sub-genus. In an embodiment within the third sub-genus, k is 0 and $Z^A$ is selected from oxadiazolyl substituted with pyridinyl under $Z^2$ and $Z^A$ is selected from hydrogen, $C_{1-6}$ alkyl, $C_{1-6}$ haloalkyl and benzyl under $Z^1$.

The invention encompasses a fourth sub-genus of compounds of Formula I wherein $Z^2$ is $C_{1-6}$alkyl and $Z^1$ is

[chemical structures]

and L is —CH$_2$—, and all other variables are as provided in the genus or first sub-genus.

Within the fourth sub-genus the invention encompasses a second class of compounds of Formula I wherein $Z^2$ is methyl, and all other variables are as provided in the fourth sub-genus.

Within the second class, the invention encompasses a first sub-class of compounds of Formula I wherein $Z^1$ is

[chemical structure]

and all other variables are as provided in the second class.

Also within the genus, the invention encompasses a fifth sub-genus of compounds of Formula I of Formula Ia (Ia)

[chemical structure]

or a pharmaceutically acceptable salt thereof, wherein $W^1$ is CH or N, and all other variables are as provided in the genus. $X^B$ and $X^C$ may be substituted on any substitutable position including, for $X^C$, $W^1$ when $W^1$ is CH.

Within the fifth sub-genus, the invention encompasses a third class of compounds of Formula Ia wherein:
$Z^2$ is methyl
R is H or fluoro,
$Y^3$ is CH or N,
$X^B$ and $X^C$ are independently selected from halo, —OCH$_3$, —CF$_3$ and —OCF$_3$, and
m and n are independently 0, 1 or 2, and all other variables are as provided in the genus.

The invention encompasses a second sub-class of compounds of Formula Ia wherein X is selected from: H, —NH$_2$ and —N(H)—C(O)—OR$^8$, and all other variables are as provided in the fifth sub-genus or third class. The invention encompasses a group of compounds of Formula Ia wherein $W^1$ is CH, one $X^B$ group is present and substituted at the 4-position, one or two $X^C$ groups are present and substituted at the 3- or 3,5-positions respectively, and the $X^B$ group is a different group with respect to either $X^C$ group, and all other variables are as provided in the fifth sub-genus or third class.

The invention encompasses a group of compounds of Formula Ia wherein $Z^A$ is selected from the group consisting of:
  (1) hydrogen,
  (2) $C_{1-10}$ alkyl,
  (3) $C_{2-10}$ alkenyl, and
  (4) $C_{3-7}$ cycloalkyl,
wherein said $C_{1-10}$ alkyl, $C_{2-10}$ alkenyl and $C_{3-7}$ cycloalky are optionally substituted with 1 to 6 substituents as allowed by valence independently selected from the group consisting of: fluoro, hydroxy, carbamoyl, $C_{3-6}$ cycloalkyl, C(O)O—$C_{1-6}$ alkyl, C(O)OH, C(O)—$C_{1-6}$ alkyl, N(H)—$C_{1-6}$ alkyl, N(—$C_{1-6}$ alkyl)$_2$, ArylA, HetA and HetB, and all other variables are as provided in the fifth sub-genus, third class or second sub-class as described above.

The invention encompasses a sub-group of compounds of Formula Ia wherein $Z^A$ is $C_{1-10}$ alkyl, optionally substituted with 1 to 6 substituents as allowed by valence independently selected from the group consisting of: fluoro and hydroxyl, and all other variables are as provided in the fifth sub-genus, third class or second sub-class as described above. The invention encompasses compounds of Formula Ia wherein $Z^A$ is —(CH$_2$)$_{0-4}$—CF$_3$, and all other variables are as provided in fifth sub-genus, third class or second sub-class as described above.

The present invention includes compounds of Formula I above and pharmaceutically acceptable salts thereof.

Compounds of Formula Ia form a subset of the compounds included in Formula I. Any description which follows that refers to a compound of Formula I also applies to a compound of Formula Ia.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c), (d) or (e) r the combination of (f) or (g).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}$ $CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

The term "aryl" refers to phenyl and naphthyl. The aryl of particular interest is phenyl.

The term "heteroaryl" refers to (i) a 5- or 6-membered heteroaromatic ring containing from 1 to 3 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention (see HetB) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and encompasses both the keto and enol forms of a compound when conversion is possible.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for reduced likelihood of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (e.g., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following routes: orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the inhibition of HIV replication, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57th edition (2003), the 58th edition (2004), or the 59th edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be used for these purposes.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Abbreviations employed herein include the following: Bn=benzyl; BOC (or Boc)=t-butyloxycarbonyl; Boc$_2$O=di-t-butyl carbonate; BOP=benzotriazol-1-yloxytris-(dimethylamino)phosphonium; BSA=bovine serum albumin; CBS=Corey, Bakshi, Shibata chiral oxazaborolidine mediated ketone reduction; Cbz=benzyloxycarbonyl; DBU=1,8-diazabicyclo[5.4.0]undec-7-one; DCAD=di-(4-chlorobenzyl) azodicarboxylate; DCE=1,2-dichloroethane; DCM=dichloromethane; DEAD=diethyl azodicarboxylate; DIAD=diisopropylazodicarboxylate; Dibal-H=diisobutylaluminum hydride; DMAP=4-dimethylaminopyridine; DMF=dimethylformamide; DMSO=dimethyl sulfoxide; EDC=1-ethyl-3-(3-dimethylaminopropyl) carbodiimide; Et=ethyl; EtOAc=ethyl acetate; EtOH=ethanol; G-2G=Grubbs catalyst, 2$^{nd}$ generation; HOAt=1-hydroxy-7-azabenzotriazole; HPLC=high performance liquid chromatography; HSU=hydroxysuccinimide; i-PrOH=isopropanol; LAH=lithium aluminum hydride; LC-MS=liquid chromatography-mass spectroscopy; Me=methyl; MeOH=methanol; MOC=methoxycarbonyl; Ms=mesyl or methanesulfonyl; NMR=nuclear magnetic resonance; Ph=phenyl; RCM=ring closing metathesis; Piv=pivaloyl; PPTS=pyridinium p-toluene sulfonate; PyBrOP=bromo-tris-pyrrolidinophosphonium hexafluorophosphate; SCX=strong cation exchange resin; STP=standard temperature and pressure (i.e., 25° C. & 1 atmosphere); TBS=tert-butyldimethylsilyl; TBDPS=tert-butyl(diphenyl) silyl; TBDPSCl=tert-butyl(dimethyl)silyl chloride; TEA=triethylamine; TFA=trifluoroacetic acid; THF=tetrahydrofuran; TLC=thin layer chromatography; TMAF=tetramethyl ammonium fluoride; TMSCHN$_2$=trimethylsilyl diazomethane; TPAP=tetrapropylammonium perruthenate; TPP=triphenylphosphine.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl optionally substituted with one or more $X^A$. In the examples that follow, when a nitrogen atom is depicted without the necessary hydrogen atoms to complete the valence, it is assumed those nitrogen atoms are present unless specifically depicted to the contrary.

Example 1

N-(2-{2-[(2R,5R,6S)-6-{[(4-chlorophenyl)sulfanyl]methyl}-5-methylmorpholin-2-yl]ethyl}phenyl)-Nα-(methoxycarbonyl)-β-phenyl-L-phenylalaninamide

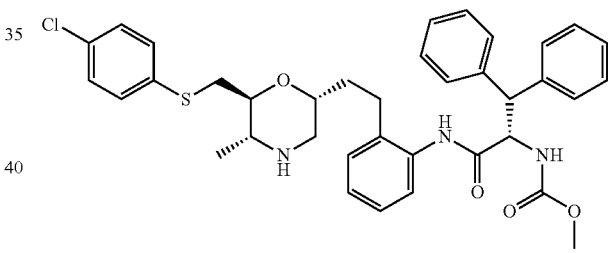

Step 1: (2Z)-but-2-en-1-ol

A solution of 2-butyn-1-ol (1 eq) in MeOH (2.9 M) was circulated in H-cube for 19 hrs at a flow of 1 mL/min. The H-Cube was used with Lindlar Catalyst cartridge (THS02114) at 25° C. and 40 bars of H$_2$. The flow was stopped and MeOH was removed under normal pressure upon heating at 60-64° C. and coevaporated twice with heptane. The resulting compound was cooled to rt and dried under reduced pressure (at 30 mm of Hg) to afford desired product.

Step 2: tert-butyl {[(2R,3S)-3-methyloxiran-2-yl]methoxy}diphenylsilane

Activated 3 A molecular sieves, (0.03 g/mmol) was introduced in a flask and the flask was flushed with nitrogen prior the addition of CH2Cl$_2$ (0.6M). The suspension was cooled to −20° C. and diisopropyl D-tartrate (0.14 eq), (2Z)-but-2-en-1-ol (1 eq) and titanium(IV) isopropoxide (0.1 eq) were sequentially added. The reaction mixture was stirred at −20° C. for 15 min. and 5M Tert-butyl hydroperoxide in decane (2 eq) was added using a glass pipette. The mixture was stirred at −20° C. for 90 minutes and then slowly warmed to 5° C. over 1 hour. $^1$H NMR of an aliquot after 2.5 hours showed 95% conversion. The reaction mixture was cooled again to −20° C., and aged for 1 hour. Excess t-BuOOH was carefully quenched at −20° C. with tri-n-butylphosphine (1 eq), and aged for 15 min. Then excess of titanium (IV) isopropoxide was quenched with a 0.1M solution of citric acid monohydrate in 10% acetone/Et$_2$O. The cooling bath was removed and the reaction mixture was aged for 25 min (it became yellow). After filtration through celite, the filtrate was concentrated to yield crude yellow oil. The crude material was dissolved in CH$_2$Cl$_2$, cooled to 0° C. and imidazole (2.4 eq) was added followed by TBDPS-Cl (1.15 eq). The reaction mixture was aged at rt overnight. CH$_2$Cl$_2$ and brine were then added, the layers were partitioned and the aqueous layer was extracted with CH$_2$Cl$_2$. The combined organic layers were washed with brine, dried over MgSO4, filtered and concentrated to dryness. The residue was purified by automated SiO$_2$ flash chromatography system using solvent gradient of 10% to 100% EtOAc/Hex to afford the desired compound.

Step 3: (2S,3R)-3-(benzylamino)-1-{[tert-butyl(diphenyl)silyl]oxy}butan-2-ol

Lithium perchlorate (7 eq) was added to a solution of tert-butyl {[(2R,3S)-3-methyloxiran-2-yl]methoxy}diphenylsilane (1 eq) and benzylamine (7 eq) in acetonitrile (0.3 M) at rt. The reaction mixture was heated to 65° C. for 5 hours. Upon cooling to rt, acetonitrile was removed in vacuo. Water and EtOAc were added, the layers were partitioned, and the aqueous layer was extracted with EtOAc. The combined organic layers were washed with water and brine, dried over MgSO4, filtered and concentrated to dryness. The residue was purified by automated SiO$_2$ flash chromatography system using solvent gradient of 20% to 100% EtOAc/Hex to afford the desired compound.

Step 4: (2S,3R)-3-{benzyl[(2R)-3-chloro-2-hydroxypropyl]amino}-1-{[tert-butyl(diphenyl)silyl]oxy}butan-2-ol To (2S,3R)-3-(benzylamino)-1-{[tert-butyl(diphenyl)silyl]oxy}butan-2-ol (1 eq) in toluene (0.2 M) at rt was added (R)-(−)-epichlorohydrin (1.6 eq) followed by the addition of lithium perchlorate (1.8 eq). The reaction mixture was heated to 70° C. for 16 hours and then cooled to rt. The material was used without further purification in the next step.

Step 5: [(2S,5R,6S)-4-benzyl-6-({[tert-butyl(diphenyl)silyl]oxy}methyl)-5-methylmorpholin-2-yl]methanol To a stirred solution of (2S,3R)-3-{benzyl[(2R)-3-chloro-2-hydroxypropyl]amino}-1-{[tert-butyl(diphenyl)silyl]oxy}butan-2-ol in toluene (1 eq) at rt was added methanol (0.4 M) added, followed by sodium methoxide (4.5 eq) 25 wt % in MeOH. The reaction mixture was aged at rt for 7 hours. More sodium methoxide (1.3 eq) was added, and aged for 17 additional hours. Aqueous saturated NH$_4$Cl was added and the aqueous layer was extracted with EtOAc. The combined organic layers were washed with brine, dried over MgSO$_4$, filtered and concentrated to dryness. The residue was purified by automated SiO$_2$ flash chromatography system using solvent gradient of 10% to 60% EtOAc/Hex to afford the desired compound.

Step 6: [(2S,5R,6S)-6-({[tert-butyl(diphenyl)silyl]oxy}methyl)-5-methylmorpholin-2-yl]methanol A mixture of [(2S,5R,6S)-4-benzyl-6-({[tert-butyl(diphenyl)silyl]oxy}methyl)-5-methylmorpholin-2-yl]methanol (1 eq) and Pd(OH)$_2$ (0.3 eq) was flushed with nitrogen, then MeOH (0.1M) was added. The suspension was placed in Parr hydrogenation apparatus overnight at 50 psi. The suspension was filtered through celite, and washed with CH$_2$Cl$_2$. The filtrate was concentrated to dryness and used in the subsequent step without further purification.

Step 7: tert-butyl (2S,3R,6S)-2-({[tert-butyl(diphenyl)silyl]oxy}methyl)-6-(hydroxymethyl)-3-methylmorpholine-4-carboxylate To a stirred solution of [(2S,5R,6S)-6-({[tert-butyl(diphenyl)silyl]oxy}methyl)-5-methylmorpholin-2-yl]methanol (1 eq) in THF (0.2M) and water (0.2M) at room temperature were added BOC$_2$O (1 eq) and sodium bicarbonate (5 eq). The reaction mixture was stirred at room temperature for 2 hours. It was poured into water and the aqueous layer was extracted with ethyl acetate. The combined organic layers were washed with brine, dried with MgSO$_4$ and concentrated under vacuum. The residue was purified by automated SiO$_2$ flash chromatography system using solvent gradient of 0% to 80% EtOAc/Hex to afford the desired compound.

Step 8: tert-butyl (2 S,3R,6S)-2-({[tert-butyl(diphenyl)silyl]oxy}methyl)-6-formyl-3-methylmorpholine-4-carboxylate To a stirred solution of oxalyl chloride (5 eq) in DCM (0.3 M) at −78° C. was added a solution of DMSO (10 eq) in DCM (0.5M). The reaction mixture was stirred at −78° C. for 30 min. A solution of tert-butyl (2S,3R,6S)-2-({[tert-butyl(diphenyl)silyl]oxy}methyl)-6-(hydroxymethyl)-3-methylmorpholine-4-carboxylate (1 eq) in CH$_2$Cl$_2$ (0.2M) was added dropwise and stirred at −40° C. for 1.5 hours. It was then cooled to −78° C. and triethylamine (10 eq)) was added and the reaction mixture was stirred at 0° C. for 1 h. Water was added and the reaction mixture was warmed to rt for 30 min. The mixture was poured into aqueous sodium hydrogen carbonate and the aqueous layer was extracted with CH$_2$Cl$_2$. The combined organic layers were washed with brine, dried with MgSO$_4$ and concentrated under vacuum to afford the title compound as a yellow gum. The material was used in the subsequent step without further purification.

Step 9: tert-butyl (2S,3R,6R)-2-({[tert-butyl(diphenyl)silyl]oxy})-3-methyl-6-[(E)-2-(2-nitrophenyl)ethenyl]morpholine-4-carboxylate To a stirred suspension of (2-nitrobenzyl)(triphenyl)phosphonium bromide.H$_2$O (2 eq) in DME (0.2M) at room temperature were added 18-Crown-6 (0.1 eq), and potassium carbonate (2.5 eq). The reaction mixture was stirred at room temperature for 15 min. A solution of tert-butyl (2S,3R,6S)-2-({[tert-butyl(diphenyl)silyl]oxy}methyl)-6-formyl-3-methylmorpholine-4-carboxylate (1 eq) in DME (0.2M) was added, the reaction mixture was stirred at rt overnight, filtered through celite and concentrated to dryness. The residue was purified by automated SiO$_2$ flash chromatography system using solvent gradient of 0% to 50% EtOAc/Hex to afford the desired compound.

Step 10: tert-butyl (2S,3R,6R)-6-[2-(2-aminophenyl)ethyl]-2-({[tert-butyl(diphenyl)silyl]oxy}methyl)-3-methylmorpholine-4-carboxylate A mixture of tert-butyl (2S,3R,6R)-2-({[tert-butyl(diphenyl)silyl]oxy}methyl)-3-methyl-6-[(E)-2-(2-nitrophenyl)ethenyl]morpholine-4-carboxylate (1 eq) and Pd/C (0.3 eq) was flushed with nitrogen and EtOAc (0.1M) was added. The suspension was stirred under hydrogen (1 atm) overnight, filtered through celite and washed with CH$_2$Cl$_2$. LCMS showed some desired material along with double bond not reduced. One part of MeOH was added followed by the addition of platinum on activated carbon Degussa type F101 RA/W (0.2 eq). The reaction mixture was stirred under hydrogen (1 atm) for 2 hours, filtered through celite and washed with CH$_2$Cl$_2$. The filtrate was concentrated to dryness to afford the title compound as a light pink gum.

Step 11: tert-butyl (2S,3R,6R)-2-({[tert-butyl(diphenyl)silyl]oxy}methyl)-6-[2-(2-{[N-(methoxycarbonyl)-β-phenyl-L-phenylalanyl]amino}phenyl)ethyl]-3-methylmorpholine-4-carboxylate To a stirred solution of tert-butyl (2S,3R,6R)-6-[2-(2-aminophenyl)ethyl]-2-({[tert-butyl(diphenyl)silyl]oxy}methyl)-3-methylmorpholine-4-carboxylate (1 eq) and N-(methoxycarbonyl)-β-phenyl-L-phenylalanine (1.5 eq) in DMF (0.1M) at 0° C. were added HATU (1.5 eq), and 2,6-lutidine (2.5 eq). The reaction mixture was stirred at room temperature overnight. It was poured into aqueous sodium hydrogen carbonate and the aqueous layer was extracted with ethyl acetate. The combined organic layers were washed with brine, dried with MgSO$_4$ and concentrated under vacuum. The residue was purified by automated SiO$_2$ flash chromatography system using solvent gradient of 0% to 60% EtOAc/Hex to afford the desired compound.

Step 12: tert-butyl (2S,3R,6R)-2-(hydroxymethyl)-6-[2-(2-{[N-(methoxycarbonyl)-β-phenyl-L-phenylalanyl]amino}phenyl)ethyl]-3-methylmorpholine-4-carboxylate To a stirred solution of tert-butyl (2S,3R,6R)-2-({[tert-butyl(diphenyl)silyl]oxy}methyl)-6-[2-(2-{[N-(methoxycarbonyl)-β-phenyl-L-phenylalanyl]amino}phenyl)ethyl]-3-methylmorpholine-4-carboxylate (1 eq) in THF (0.1 M) at room temperature was added TBAF (2 eq). The reaction mixture was stirred at room temperature for 2 hours. It was poured into water and the aqueous layer was extracted with ethyl acetate. The combined organic layers were washed with brine, dried with MgSO$_4$ and concentrated under vacuum. The residue was purified by automated SiO$_2$ flash chromatography system using solvent gradient of 0% to 90% EtOAc/Hex to afford the desired compound.

Step 13: tert-butyl (2S,3R,6R)-2-{[(4-chlorophenyl)sulfanyl]methyl}-6-[2-(2-{[N-(methoxycarbonyl)-β-phenyl-L-phenylalanyl]amino}phenyl)ethyl]-3-methylmorpholine-4-carboxylate A solution of tert-butyl (2S,3R,6R)-2-(hydroxymethyl)-6-[2-(2-{[N-(methoxycarbonyl)-β-phenyl-L-phenylalanyl]amino}phenyl)ethyl]-3-methylmorpholine-4-carboxylate (1 eq) and 4-chlorothiophenol (2 eq) in benzene (0.1M) was bubbled with nitrogen and cyanomethylenetributylphosphorane (2 eq) was added, the reaction mixture was heated at 100° C. for 1 hour. The reaction mixture was concentrated to dryness and the residue was purified by automated SiO$_2$ flash chromatography system using solvent gradient of 0% to 60% EtOAc/Hex to afford the desired compound.

Step 14: N-(2-{2-[(2R,5R,6S)-6-{[(4-chlorophenyl)sulfanyl]methyl}-5-methylmorpholin-2-yl]ethyl}phenyl)-Nα-(methoxycarbonyl)-β-phenyl-L-phenylalaninamide Tert-butyl (2S,3R,6R)-2-{[(4-chlorophenyl)sulfanyl]methyl}-6-[2-(2-{[N-(methoxycarbonyl)-β-phenyl-L-phenylalanyl]amino}phenyl)ethyl]-3-methylmorpholine-4-carboxylate in a 1:1 mixture of CH$_2$Cl$_2$/TFA (0.1 M) was stirred at rt for 1 hr. The reaction mixture was concentrated under reduced pressure and the residue was co-evaporated twice with heptane and triturated in Et$_2$O to afford the desired product as a TFA salt. Alternatively, the TFA salt, after concentration, could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH2Cl2 to afford the desired compound. Alternatively, the free base could be purified by filtration on SCX SPE cartridge made of pTSA-SiO$_2$ eluted first with MeOH to remove non basic impurities and eluted then with 10% NH$_4$OH/MeOH to elute the free base and afford the desired compound after concentration under reduced pressure.

M+1, +ESI=658

Examples 2 to 29 were prepared using the appropriate phenol or thiophenol and by following the procedures described in Example 1

| Example | | Compound name | Characteriz. data |
|---|---|---|---|
| 2 | 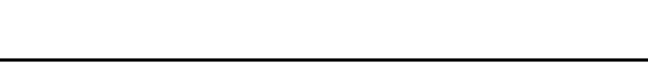 | N-(2-{2-[(2R,5R,6S)-6-{[(4-cyanophenyl)sulfanyl]methyl}-5-methylmorpholin-2-yl]ethyl}phenyl)-Nα-(methoxycarbonyl)-β-phenyl-L-phenylalaninamide | M + 1 = 633 |

-continued

| Example | Compound name | Characteriz. data |
|---|---|---|
| 3 | N-(2-{2-[(2R,5R,6S)-6-{[(3-chloropyridin-2-yl)sulfanyl]methyl}-5-methylmorpholin-2-yl]ethyl}phenyl)-Nα-(methoxycarbonyl)-β-phenyl-L-phenylalaninamide | M + 1 = 659 |
| 4 | methyl [(2S)-1-{[2-(2-{(2R,5R,6S)-5-methyl-6-[(quinolin-5-ylsulfanyl)methyl]morpholin-2-yl}ethyl)phenyl]amino}-1-oxo-3,3-diphenylpropan-2-yl]carbamate | M + 1 = 697 |
| 5 | methyl N-[(1S)-1-benzhydryl-2-[[2-[2-[(2R,5R,6S)-5-methyl-6-[[5-(4-pyridyl)-1,3,4-oxadiazol-2-yl]sulfanylmethyl]morpholin-2-yl]ethyl]phenyl]amino]-2-oxo-ethyl]carbamate | M + 1 = 693.3 |
| 6 | methyl N-[(1S)-1-benzhydryl-2-[[2-[2-[(2R,5R,6S)-5-methyl-6-[[5-[(5-methylpyrazol-1-yl)methyl]-1,3,4-oxadiazol-2-yl]sulfanylmethyl]morpholin-2-yl]ethyl]phenyl]amino]-2-oxo-ethyl]carbamate | M + 1 = 710.3 |
| 7 | methyl N-[(1S)-1-benzhydryl-2-[[2-[2-[(2R,5R,6S)-5-methyl-6-[[5-[(2-methylthiazol-4-yl)methyl]-1,3,4-oxadiazol-2-yl]sulfanylmethyl]morpholin-2-yl]ethyl]phenyl]amino]-2-oxo-ethyl]carbamate | M + 1 = 727.3 |

| Example | | Compound name | Characteriz. data |
|---|---|---|---|
| 8 | 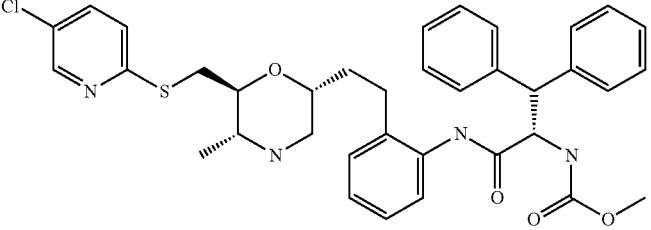 [SMILES: COC(=O)N[C@H](C(=O)Nc1ccccc1CC[C@@H]1CN[C@H](C)[C@@H](CSc2ccc(Cl)cn2)O1)C(c1ccccc1)c1ccccc1] | methyl N-[(1S)-1-benzhydryl-2-[[2-[2-[(2R,5R,6S)-6-[(5-chloro-2-pyridyl)sulfanylmethyl]-5-methyl-morpholin-2-yl]ethyl]phenyl]amino]-2-oxo-ethyl]carbamate | M + 1 = 659.2 |
| 9 | 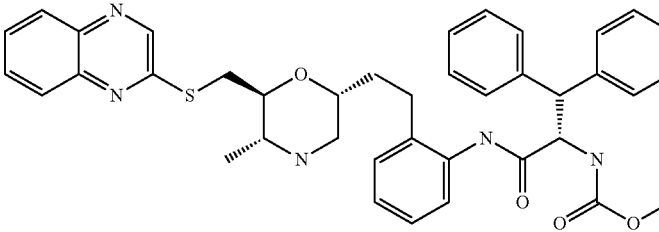 | methyl N-[(1S)-1-benzhydryl-2-[[2-[2-[(2R,5R,6S)-5-methyl-6-(quinoxalin-2-ylsulfanylmethyl)morpholin-2-yl]ethyl]phenyl]amino]-2-oxo-ethyl]carbamate | M + 1 = 676.3 |
| 10 | 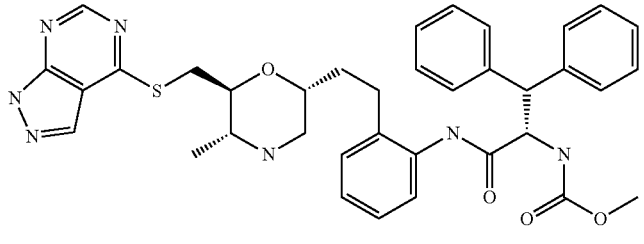 [SMILES: COC(=O)N[C@H](C(=O)Nc1ccccc1CC[C@@H]1CN[C@H](C)[C@@H](CSc2ncnc3[nH]ncc23)O1)C(c1ccccc1)c1ccccc1] | methyl N-[(1S)-1-benzhydryl-2-[[2-[2-[(2R,5R,6S)-5-methyl-6-(1H-pyrazolo[3,4-d]pyrimidin-4-ylsulfanylmethyl)morpholin-2-yl]ethyl]phenyl]amino]-2-oxo-ethyl]carbamate | M + 1 = 666.3 |
| 11 | 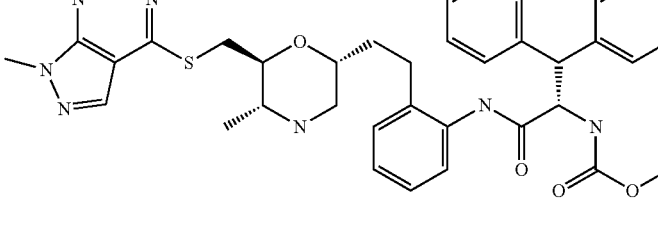 | methyl N-[(1S)-1-benzhydryl-2-[[2-[2-[(2R,5R,6S)-5-methyl-6-[(1-methylpyrazolo[3,4-d]pyrimidin-4-yl)sulfanylmethyl]morpholin-2-yl]ethyl]phenyl]amino]-2-oxo-ethyl]carbamate | M + 1 = 680.3 |
| 12 | 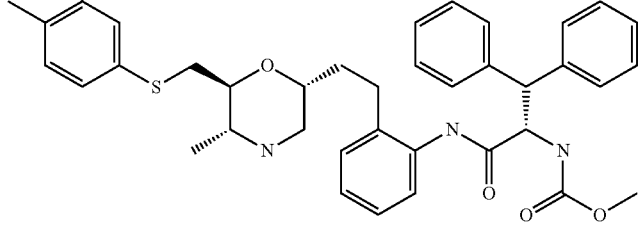 | methyl N-[(1S)-1-benzhydryl-2-[[2-[2-[(2R,5R,6S)-6-[(3,4-dimethylphenyl)sulfanylmethyl]-5-methyl-morpholin-2-yl]ethyl]phenyl]amino]-2-oxo-ethyl]carbamate | M + 1 = 652.3 |
| 13 | 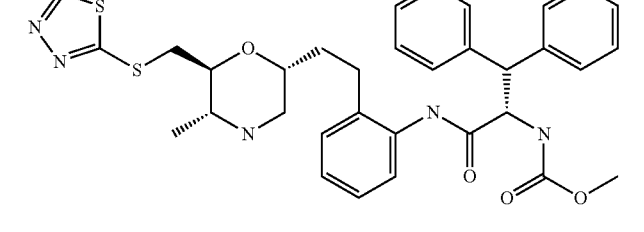 | methyl N-[(1S)-1-benzhydryl-2-[[2-[2-[(2R,5R,6S)-5-methyl-6-(1,3,4-thiadiazol-2-ylsulfanylmethyl)morpholin-2-yl]ethyl]phenyl]amino]-2-oxo-ethyl]carbamate | M + 1 = 632.3 |

-continued

| Example | | Compound name | Characteriz. data |
|---|---|---|---|
| 14 | 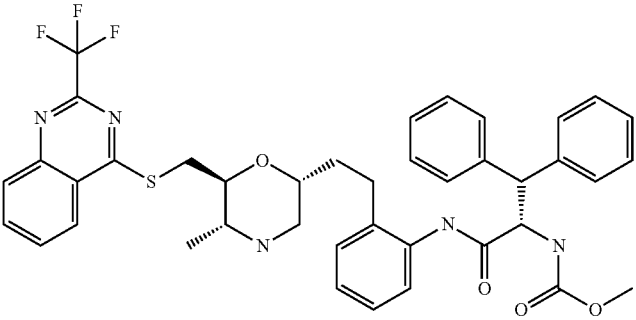 [SMILES: COC(=O)N[C@H](C(=O)Nc1ccccc1CC[C@@H]1CN[C@H](C)[C@@H](CSc2nc(C(F)(F)F)nc3ccccc23)O1)C(c1ccccc1)c1ccccc1] | methyl N-[(1S)-1-benzhydryl-2-[[2-[2-[(2R,5R,6S)-5-methyl-6-[[2-(trifluoromethyl)quinazolin-4-yl]sulfanylmethyl]morpholin-2-yl]ethyl]phenyl]amino]-2-oxo-ethyl]carbamate | M + 1 = 744.3 |
| 15 | 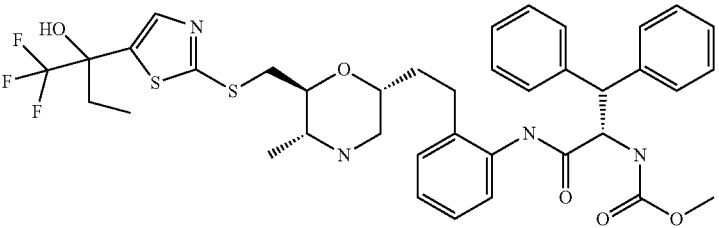 [SMILES: CCC(O)(c1cnc(SC[C@H]2O[C@H](CCc3ccccc3NC(=O)[C@@H](NC(=O)OC)C(c3ccccc3)c3ccccc3)CN[C@@H]2C)s1)C(F)(F)F] | methyl N-[(1S)-1-benzhydryl-2-[[2-[2-[(2R,5R,6S)-6-[[5-[1-hydroxy-1-(trifluoromethyl)propyl]thiazol-2-yl]sulfanylmethyl]-5-methyl-morpholin-2-yl]ethyl]phenyl]amino]-2-oxo-ethyl]carbamate | M + 1 = 757.3 |
| 16 | 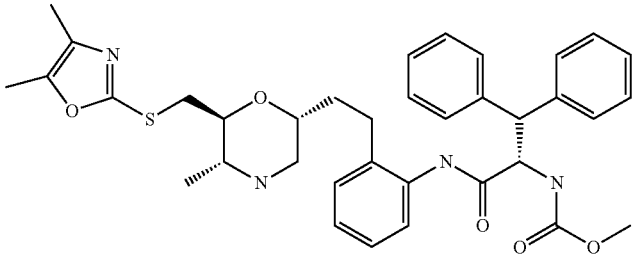 | methyl N-[(1S)-1-benzhydryl-2-[[2-[2-[(2R,5R,6S)-6-[(4,5-dimethyloxazol-2-yl)sulfanylmethyl]-5-methyl-morpholin-2-yl]ethyl]phenyl]amino]-2-oxo-ethyl]carbamate | M + 1 = 643.3 |
| 17 | 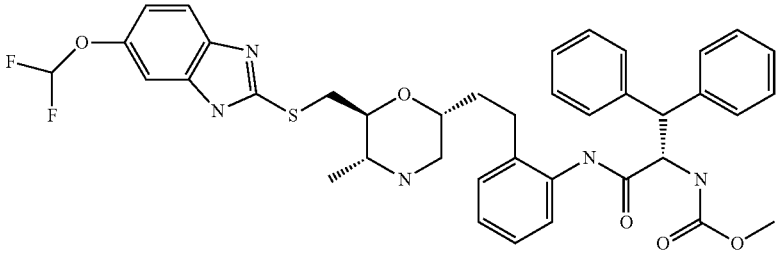 [SMILES: COC(=O)N[C@H](C(=O)Nc1ccccc1CC[C@@H]1CN[C@H](C)[C@@H](CSc2nc3ccc(OC(F)F)cc3[nH]2)O1)C(c1ccccc1)c1ccccc1] | methyl N-[(1S)-1-benzhydryl-2-[[2-[2-[(2R,5R,6S)-6-[[5-(difluoromethoxy)-1H-benzimidazol-2-yl]sulfanylmethyl]-5-methyl-morpholin-2-yl]ethyl]phenyl]amino]-2-oxo-ethyl]carbamate | M + 1 = 730.3 |
| 18 | 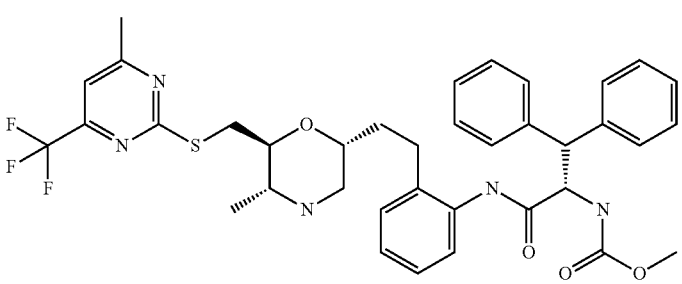 [SMILES: COC(=O)N[C@H](C(=O)Nc1ccccc1CC[C@@H]1CN[C@H](C)[C@@H](CSc2nc(C)cc(C(F)(F)F)n2)O1)C(c1ccccc1)c1ccccc1] | methyl N-[(1S)-1-benzhydryl-2-[[2-[2-[(2R,5R,6S)-5-methyl-6-[[4-methyl-6-(trifluoromethyl)pyrimidin-2-yl]sulfanylmethyl]morpholin-2-yl]ethyl]phenyl]amino]-2-oxo-ethyl]carbamate | M + 1 = 708.3 |

-continued

| Example | | Compound name | Characteriz. data |
|---|---|---|---|
| 19 | 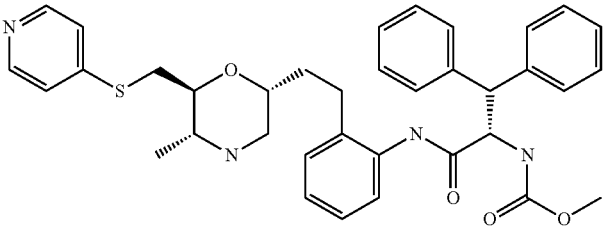 [SMILES: COC(=O)N[C@H](C(=O)Nc1ccccc1CC[C@@H]1CN[C@H](C)[C@@H](CSc2ccncc2)O1)C(c1ccccc1)c1ccccc1] | methyl N-[(1S)-1-benzhydryl-2-[[2-[2-[(2R,5R,6S)-5-methyl-6-(4-pyridylsulfanylmethyl)morpholin-2-yl]ethyl]phenyl]amino]-2-oxo-ethyl]carbamate | M + 1 = 625.3 |
| 20 | 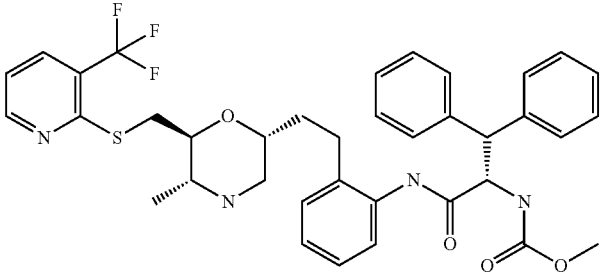 [SMILES: COC(=O)N[C@H](C(=O)Nc1ccccc1CC[C@@H]1CN[C@H](C)[C@@H](CSc2ncccc2C(F)(F)F)O1)C(c1ccccc1)c1ccccc1] | methyl N-[(1S)-1-benzhydryl-2-[[2-[2-[(2R,5R,6S)-5-methyl-6-[[3-(trifluoromethyl)-2-pyridyl]sulfanylmethyl]morpholin-2-yl]ethyl]phenyl]amino]-2-oxo-ethyl]carbamate | M + 1 = 693.3 |
| 21 | 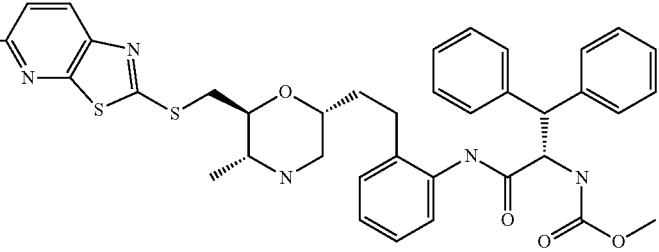 | methyl N-[(1S)-1-benzhydryl-2-[[2-[2-[(2R,5R,6S)-6-[(5-chlorothiazolo[5,4-b]pyridin-2-yl)sulfanylmethyl]-5-methyl-morpholin-2-yl]ethyl]phenyl]amino]-2-oxo-ethyl]carbamate | M + 1 = 716.2 |
| 22 | 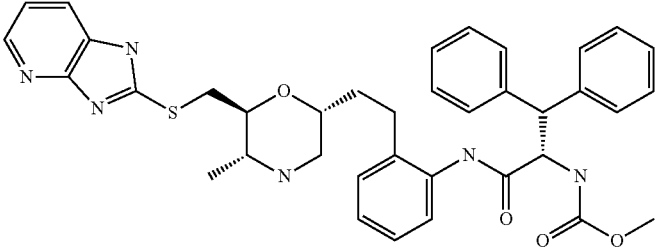 [SMILES: COC(=O)N[C@H](C(=O)Nc1ccccc1CC[C@@H]1CN[C@H](C)[C@@H](CSc2nc3ncccc3[nH]2)O1)C(c1ccccc1)c1ccccc1] | methyl N-[(1S)-1-benzhydryl-2-[[2-[2-[(2R,5R,6S)-6-(1H-imidazo[4,5-b]pyridin-2-ylsulfanylmethyl)-5-methyl-morpholin-2-yl]ethyl]phenyl]amino]-2-oxo-ethyl]carbamate | M + 1 = 665.3 |
| 23 | 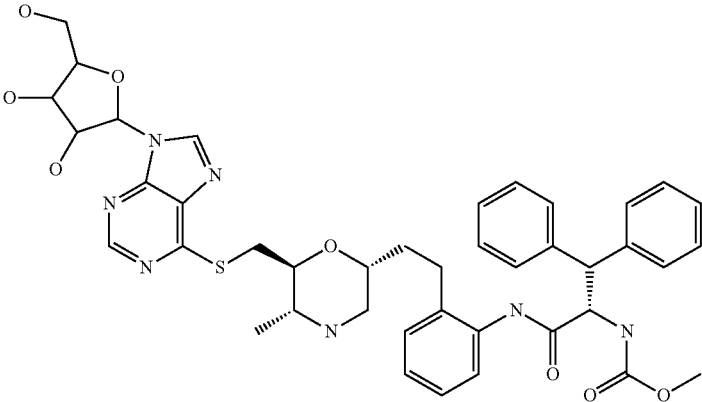 [SMILES: COC(=O)N[C@H](C(=O)Nc1ccccc1CC[C@@H]1CN[C@H](C)[C@@H](CSc2ncnc3c2ncn3C2OC(CO)C(O)C2O)O1)C(c1ccccc1)c1ccccc1] | methyl N-[(1S)-1-benzhydryl-2-[[2-[2-[(2R,5R,6S)-6-[[9-[(2R,3R,4S,5R)-3,4-dihydroxy-5-(hydroxymethyl)tetrahydrofuran-2-yl]purin-6-yl]sulfanylmethyl]-5-methyl-morpholin-2-yl]ethyl]phenyl]amino]-2-oxo-ethyl]carbamate | M + 1 = 798.3 |

-continued

| Example | | Compound name | Characteriz. data |
|---|---|---|---|
| 24 | 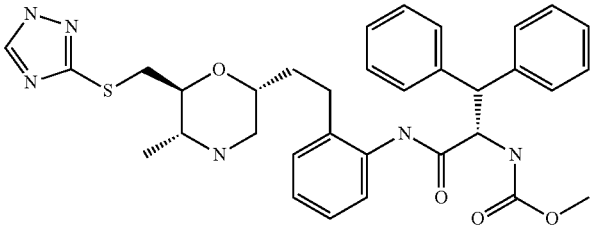 [SMILES: COC(=O)N[C@H](C(=O)Nc1ccccc1CC[C@@H]1CN[C@H](C)[C@@H](CSc2nc[nH]n2)O1)C(c1ccccc1)c1ccccc1] | methyl N-[(1S)-1-benzhydryl-2-[[2-[2-[(2R,5R,6S)-5-methyl-6-(1H-1,2,4-triazol-3-ylsulfanylmethyl)morpholin-2-yl]ethyl]phenyl]amino]-2-oxo-ethyl]carbamate | M + 1 = 615.3 |
| 25 | 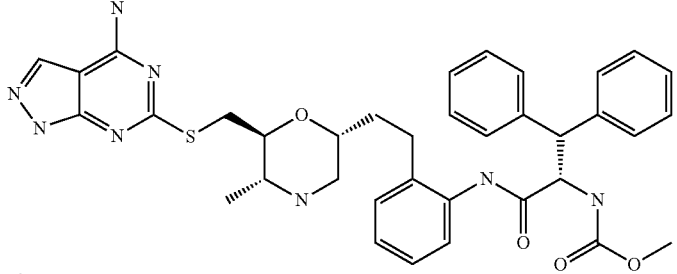 [SMILES: COC(=O)N[C@H](C(=O)Nc1ccccc1CC[C@@H]1CN[C@H](C)[C@@H](CSc2nc(N)c3cn[nH]c3n2)O1)C(c1ccccc1)c1ccccc1] | methyl N-[(1S)-1-[[2-[2-[(2R,5R,6S)-6-[(4-amino-1H-pyrazolo[3,4-d]pyrimidin-6-yl)sulfanylmethyl]-5-methyl-morpholin-2-yl]ethyl]phenyl]carbamoyl]-2,2-diphenyl-ethyl]carbamate | M + 1 = 681.3 |
| 26 | 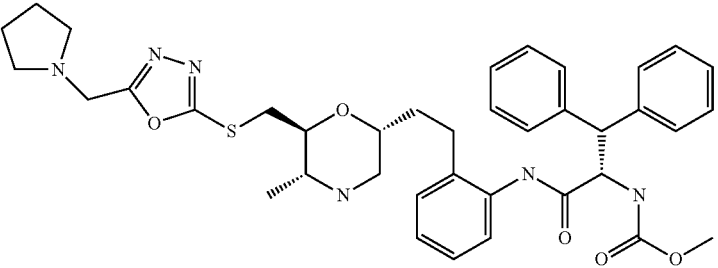 [SMILES: COC(=O)N[C@H](C(=O)Nc1ccccc1CC[C@@H]1CN[C@H](C)[C@@H](CSc2nnc(CN3CCCC3)o2)O1)C(c1ccccc1)c1ccccc1] | methyl N-[(1S)-1-benzhydryl-2-[[2-[2-[(2R,5R,6S)-5-methyl-6-[[5-(pyrrolidin-1-ylmethyl)-1,3,4-oxadiazol-2-yl]sulfanylmethyl]morpholin-2-yl]ethyl]phenyl]amino]-2-oxo-ethyl]carbamate | M + 1 = 699.3 |
| 27 | 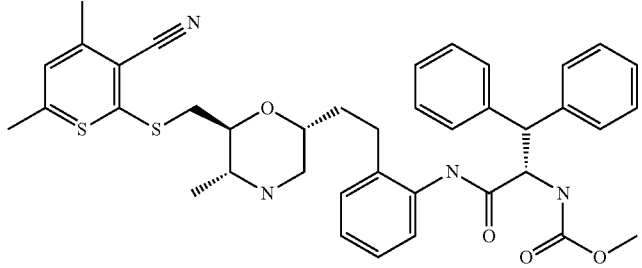 | methyl N-[(1S)-1-benzhydryl-2-[[2-[2-[(2R,5R,6S)-6-[(3-cyano-4,6-dimethyl-2-pyridyl)sulfanylmethyl]-5-methyl-morpholin-2-yl]ethyl]phenyl]amino]-2-oxo-ethyl]carbamate | M + 1 = 678.3 |
| 28 | 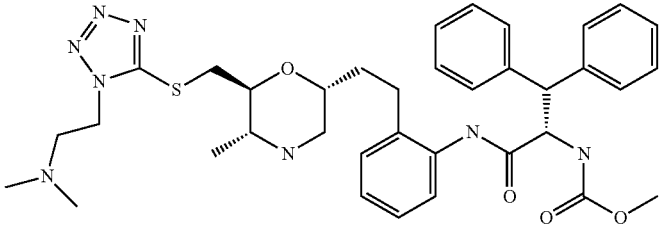 | methyl N-[(1S)-1-benzhydryl-2-[[2-[2-[(2R,5R,6S)-6-[[1-(2-dimethylaminoethyl)tetrazol-5-yl]sulfanylmethyl]-5-methyl-morpholin-2-yl]ethyl]phenyl]amino]-2-oxo-ethyl]carbamate | M + 1 = 687.3 |
| 29 | 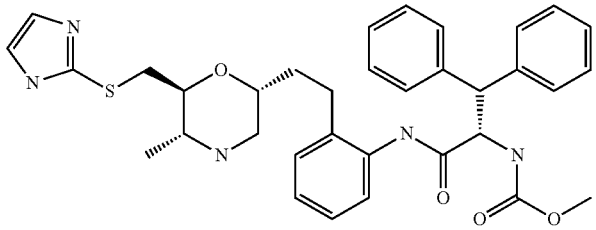 [SMILES: COC(=O)N[C@H](C(=O)Nc1ccccc1CC[C@@H]1CN[C@H](C)[C@@H](CSc2ncc[nH]2)O1)C(c1ccccc1)c1ccccc1] | methyl N-[(1S)-1-benzhydryl-2-[[2-[2-[(2R,5R,6S)-6-(1H-imidazol-2-ylsulfanylmethyl)-5-methyl-morpholin-2-yl]ethyl]phenyl]amino]-2-oxo-ethyl]carbamate | M + 1 = 614.3 |

Example 30

[(2S,3R,6R)-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholin-3-yl]methyl acetate

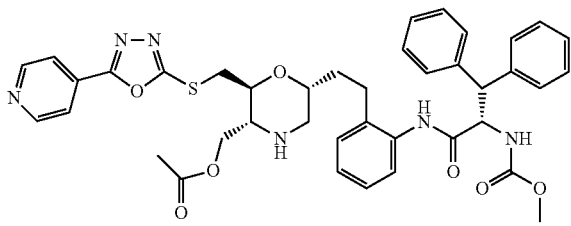 [SMILES: COC(=O)N[C@H](C(=O)Nc1ccccc1CC[C@@H]1CN[C@H](COC(C)=O)[C@@H](CSc2nnc(-c3ccncc3)o2)O1)C(c1ccccc1)c1ccccc1]

Step 1: {(2R,3S)-3-[(benzyloxy)methyl]oxiran-2-yl}methanol

Molecular sieves 4 A (0.05 g/mmol) were introduced in the flask, flushed with nitrogen. Then DCM (0.3 M) was added, cooled to −20° C., cis-4-benzyloxy-2-buten-1-ol (5 mL, 29.7 mmol), (−)-diethyl d-tartrate (0.01 eq) in DCM (0.2M), and titanium(iv) isopropoxide (0.1 eq) were sequentially added. The reaction mixture was stirred at −20° C. for 15 min. Tert-butyl hydroperoxide (2 eq) was added using a glass pipette (no needle). Then the reaction mixture was stirred at −24° C. over 72 hrs. Excess of t-BuOOH was carefully quenched at −20° C. with tri-n-butylphosphine (1 eq), aged for 15 min. Then the excess of titanium was quenched with a 9:1 diethyl ether/acetone solution of 0.05M citric acid. The cooling bath was removed and the reaction mixture was aged for 25 min (became yellow). The reaction mixture was filtered over celite, and the filtrate was concentrated to yield crude yellow oil. Chiral HPLC: ~83% ee on crude. Chiralpak 250×4.6 mm, 95% hexanes/i-PrOH, 20 min, 10 uL, 35° C., λ 210 nm, 0.9 mL/min.
The residue was purified by column chromatography on silica gel using automatized gradiant pump system CombiFlash eluting with ethyl acetate/hexanes (0:100 to 100:0) to give the title compound.

Step 2: ({(2R,3S)-3-[(benzyloxy)methyl]oxiran-2-yl}methoxy)(tert-butyl)diphenylsilane To a solution of {(2R,3S)-3-[(benzyloxy)methyl]oxiran-2-yl}methanol (2.87 g, 13.59 mmol) in DCM (0.4M) at 0° C. was added imidazole (4 eq) and TBDPS-Cl (1.4 eq). The reaction mixture was stirred at rt for 16 hrs. DCM and brine were added to the reaction mixture, and partitioned. The organic layer was dried over Na₂SO₄, filtered and concentrated to dryness. The residue was purified by column chromatography on silica gel using automatized gradiant pump system CombiFlash eluting with ethyl acetate/hexanes.

Step 3: (2S,3R)-3-(benzylamino)-4-(benzyloxy)-1-{[tert-butyl(diphenyl)silyl]oxy}butan-2-ol To a solution of ({(2R,3S)-3-[(benzyloxy)methyl]oxiran-2-yl}methoxy)(tert-butyl)diphenylsilane (1 eq) in acetonitrile (0.1M) at rt was added benzylamine (1.5 eq) and lithium perchlorate (0.5 eq). The reaction mixture was heated at 70° C. overnight, and evaporated to dryness. The residue was purified by column chromatography on silica gel using automatized gradiant pump system CombiFlash eluting with ethyl acetate/hexanes (0:100 to 100:0) to give the title compound.

Step 4: [(2S,5R,6S)-4-benzyl-5-[(benzyloxy)methyl]-6-({[tert-butyl(diphenyl)silyl]oxy}methyl)morpholin-2-yl]methanol To a solution of (2S,3R)-3-(benzylamino)-4-(benzyloxy)-1-{[tert-butyl(diphenyl)silyl]oxy}butan-2-ol (1 eq) in toluene (0.7 M) at rt was added (r)-(−)-epichlorohydrin (1.7 eq) and lithium perchlorate (2 eq). The reaction mixture was heat at 70° C. for 7 hours. Then the reaction was cooled to rt, then MeOH (0.7 M) and sodium methoxide 25% in MeOH (4.4 eq) were added and the reaction mixture was stirred at rt for 16 hrs. The reaction mixture was poured into aqueous saturated ammonium chloride, extracted with ethyl acetate (3×). The combined organic layers were washed with brine, dried over Na₂SO₄, filtered and concentrated to dryness. The residue was purified by column chromatography on silica gel using automatized gradiant pump system CombiFlash eluting with ethyl acetate/hexanes (0:100 to 100:0) to give the title compound.

Step 5: (2S,5R,6S)-4-benzyl-5-[(benzyloxy)methyl]-6-({[ten-butyl(diphenyl)silyl]oxy}methyl)morpholine-2-carbaldehyde To a stirred solution of oxalyl chloride (5 eq) in DCM (0.5M) at −78° C. was added a solution of DMSO (10 eq) in DCM (0.5M). The reaction mixture was stirred at −78° C. for 30 min. A solution of [(2S,5R,6S)-4-benzyl-5-[(benzyloxy)methyl]-6-({[tert-butyl(diphenyl)silyl]oxy}methyl)morpholin-2-yl]methanol (1 eq) in DCM (0.2M) was added dropwise, the reaction mixture was stirred at −40° C. for 1.5 hours. The reaction mixture was then cooled to −78° C. and triethylamine (10 eq) was added, stirred at 0° C. for 1 h. Water was added and the mixture warmed to rt for 30 min. The reaction mixture was poured into aqueous saturated sodium hydrogen carbonate and extracted with DCM. The combined organic layers were washed with brine, dried with MgSO₄ and concentrated under vacuum to afford the title compound as a yellow gum. This residue is used in next step without further purification.

Step 6: (2S,3R,6R)-4-benzyl-3-[(benzyloxy)methyl]-2-({[tert-butyl(diphenyl)silyl]oxy}methyl)-6-[(E)-2-(2-nitrophenyl)ethenyl]morpholine To a stirred suspension of (2-nitrobenzyl)(triphenyl)phosphonium bromide.H₂O (2 eq) in DME (0.2M) at room temperature were added 18-Crown-6 (0.1 eq), and potassium carbonate (2.2 eq). The reaction mixture was stirred at room temperature for 15 min. A solution of (2S,5R,6S)-4-benzyl-5-[(benzyloxy)methyl]-6-({[tert-butyl(diphenyl)silyl]oxy}methyl)morpholine-2-carbaldehyde (1 eq) in DME (0.2M) was added, the reaction mixture was stirred at rt for 72 hours. The mixture was filtered through celite and concentrated to dryness. The residue was purified by column chromatography on silica gel using automatized gradiant pump system CombiFlash eluting with ethyl acetate/hexanes (0:100 to 50:50) to give the title compound as a light yellow liquid. NMR showed two geometric isomers with 10:1 E/Z ratio.

Step 7: 2-{(E)-2-[(2R,5R,6S)-4-benzyl-5-[(benzyloxy)methyl]-6-({[tert-butyl(diphenyl)silyl]oxy}methyl)morpholin-2-yl]ethenyl}aniline To a stirred solution of (2S,3R,6R)-4-benzyl-3-[(benzyloxy)methyl]-2-({[tert-butyl(diphenyl)silyl]oxy}methyl)-6-[(E)-2-(2-nitrophenyl)ethenyl]morpholine (1 eq) in water (0.3M) and EtOH (0.15M) at room temperature were added iron (10 eq), and ammonium chloride (1 eq). The reaction mixture was stirred at 90° C. for 1 h. Upon cooling to rt, the reaction mixture was filtered through celite, the filtrate was concentrated in vacuo to remove ethanol. The residue was partitioned between water diluted with EtOAc, and the aqueous was extracted with ethyl acetate (2×30 mL). The combined organic layers were washed with brine, dried with $MgSO_4$ and concentrated under vacuum to afford the title compound as a yellow oil. The material is used in next step without further purification.

Step 8: N-(2-{(E)-2-[(2R,5R,6S)-4-benzyl-5-[(benzyloxy)methyl]-6-({[tert-butyl(diphenyl)silyl]oxy}methyl)morpholin-2-yl]ethenyl}phenyl)-Nα-(methoxycarbonyl)-β-phenyl-L-phenylalaninamide To a stirred solution of 2-{(E)-2-[(2R,5R,6S)-4-benzyl-5-[(benzyloxy)methyl]-6-({[tert-butyl(diphenyl)silyl]oxy}methyl)morpholin-2-yl]ethenyl}aniline (1 eq) in DMF (0.15 M) at room temperature were added N-(methoxycarbonyl)-β-phenyl-L-phenylalanine (1.5 eq), HATU (1.5 eq) and 2,6-lutidine (3 eq). The reaction mixture was stirred at room temperature overnight. It was poured into aqueous sodium hydrogen carbonate and extracted with ethyl acetate. The combined organic layers were washed with brine, dried with $MgSO_4$ and concentrated under vacuum. The residue was purified by column chromatography on silica gel using automatized gradiant pump system CombiFlash eluting with ethyl acetate/hexanes (0:100 to 60:40) to afford the title compound as a colorless foam. NMR showed two geometric isomers with 10:1 E/Z ratio.

Step 9: tert-butyl (2S,3R,6R)-3-[(benzyloxy)methyl]-2-({[tert-butyl(diphenyl)silyl]oxy}methyl)-6-[2-(2-{[N-(methoxycarbonyl)-β-phenyl-L-phenylalanyl]amino}phenyl)ethyl]morpholine-4-carboxylate A solution of N-(2-{(E)-2-[(2R,5R,6S)-4-benzyl-5-[(benzyloxy)methyl]-6-({[ten-butyl(diphenyl)silyl]oxy}methyl)morpholin-2-yl]ethenyl}phenyl)-Nα-(methoxycarbonyl)-β-phenyl-L-phenylalaninamide (1 eq), 10% Pd/C (0.6 eq), 20% $Pd(OH)_2$/C (0.5 eq) and $BOC_2O$ (5 eq) in $CF_3CH_2OH$ (0.1 M) was placed in Parr hydrogenation apparatus at 50 psi for 36 hours. LCMS showed complete reaction. The reaction mixture was filtered through celite, and washed with DCM. The filtrate was concentrated to dryness. The residue was purified by column chromatography on silica gel using automatized gradiant pump system CombiFlash eluting with ethyl acetate/hexanes (0:100 to 60:40) to give the tile compound a colorless foam.

Step 10: tert-butyl (2S,3R,6R)-2-({[tert-butyl(diphenyl)silyl]oxy}methyl)-3-(hydroxymethyl)-6-[2-(2-{[N-(methoxycarbonyl)-β-phenyl-L-phenylalanyl]amino}phenyl)ethyl]morpholine-4-carboxylate To a stirred solution of tert-butyl (2S,3R,6R)-3-[(benzyloxy)methyl]-2-({[ten-butyl(diphenyl)silyl]oxy}methyl)-6-[2-(2-{[N-(methoxycarbonyl)-β-phenyl-L-phenylalanyl]amino}phenyl)ethyl]morpholine-4-carboxylate (1 eq) in DCM (0.1M) and water (1M) was added DDQ (5 eq). The reaction mixture was stirred at rt for 32 hrs. LCMS showed about 80% conversion. The mixture was poured into aqueous saturated sodium hydrogen carbonate and extracted with ethyl acetate. The combined organic layers were washed with saturated aqueous $NaHSO_3$ and brine, dried with $MgSO_4$ and concentrated under vacuum. The residue was purified by column chromatography on silica gel using automatized gradiant pump system CombiFlash eluting with ethyl acetate/hexanes (0:100 to 80:40) to give the title compound as a light yellow foam.

Step 11: tert-butyl (2S,3R,6R)-3-[(acetyloxy)methyl]-2-(hydroxymethyl)-6-[2-(2-{[N-(methoxycarbonyl)-β-phenyl-L-phenylalanyl]amino}phenyl)ethyl]morpholine-4-carboxylate To a stirred solution of tert-butyl (2S,3R,6R)-2-({[tert-butyl(diphenyl)silyl]oxy}methyl)-3-(hydroxymethyl)-6-[2-(2-{[N-(methoxycarbonyl)-β-phenyl-L-phenylalanyl]amino}phenyl)ethyl]morpholine-4-carboxylate (1 eq) in DCM (0.2 M) at 0° C. were added $Ac_2O$ (1.3 eq)), and triethylamine (2.5 eq). The reaction mixture was stirred at room temperature for 2 h. It was poured into aqueous sodium hydrogen carbonate and extracted with DCM. The combined organic layers were washed with brine, dried with $MgSO_4$ and concentrated under vacuum to afford. The residue was dissolved in of THF (0.1M) and TBAF (1.5 eq) was added, the reaction mixture was stirred at rt for 2 hours. The mixture was poured into water and extracted with ethyl acetate. The combined organic layers were washed with brine, dried with $MgSO_4$ and concentrated under vacuum. The residue was purified by column chromatography on silica gel using automatized gradiant pump system CombiFlash eluting with ethyl acetate/hexanes (0:100 to 100:0) to give the title compound as a colorless foam.

Step 12: tert-butyl (2S,3R,6R)-3-[(acetyloxy)methyl]-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate A solution of N-{2-[(3S)-3-{[(2S,3R)-3-[(tert-butoxycarbonyl)amino]-1-hydroxy-4-(prop-1-en-2-yloxy)butan-2-yl]oxy}butyl]phenyl}-Nα-(methoxycarbonyl)-β-phenyl-L-phenylalaninamide (1 eq) and 5-(pyridin-4-yl)-1,3,4-oxadiazole-2-thiol (2 eq) in benzene (0.1M) was bubbled with nitrogen and cyanomethylenetributylphosphorane (2 eq) was added, heated at 100° C. for 1 hour. LCMS showed no complete reaction. Additional 5-(pyridin-4-yl)-1,3,4-thiadiazole-2-thiol (2 eq) and cyanomethylenetributylphosphorane (2 eq) were added, stirred at 100° C. for 4 hours. The reaction mixture was concentrated to dryness and the residue was purified by column chromatography on silica gel using automatized gradiant pump system CombiFlash eluting with ethyl acetate/hexanes (0:100 to 100:0) to give the title compound as a light yellow foam.

Step 13: [(2S,3R,6R)-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholin-3-yl]methyl acetate

[(2S,3R,6R)-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholin-3-yl]methyl acetate was prepared from tert-butyl (2S,3R,6R)-3-[(acetyloxy)methyl]-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate by following procedure described in Example 1.

M+1, +ESI=751

Example 31

N-(2-{2-[(2R,5R,6S)-5-(hydroxymethyl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide

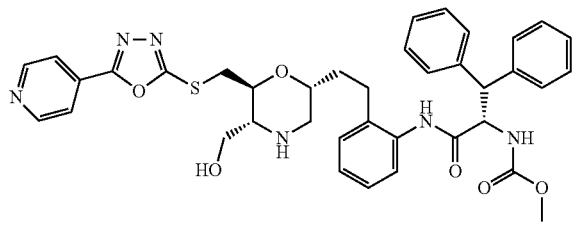 [SMILES: COC(=O)N[C@H](C(=O)Nc1ccccc1CC[C@@H]1CN[C@H](CO)[C@@H](CSc2nnc(-c3ccncc3)o2)O1)C(c1ccccc1)c1ccccc1]

Step 1: N-(2-{2-[(2R,5R,6S)-5-(hydroxymethyl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide To a stirred solution of tert-butyl (2S,3R,6R)-3-[(acetyloxy)methyl]-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate (89 mg, 0.105 mmol) in methanol (0.1M) at room temperature was added potassium carbonate (0.1 eq)). The reaction mixture was stirred at room temperature for 1 h. Aqueous saturated NH₄Cl was added, methanol was removed in vacuo, the mixture was extracted with ethyl acetate. The combined organic layers were washed with brine, dried with MgSO₄ and concentrated under vacuum. The residue was purified by column chromatography on silica gel using automatized gradiant pump system CombiFlash eluting with ethyl acetate/hexanes (0:100 to 100:0) to give tert-butyl (2S,3R,6R)-3-(hydroxymethyl)-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate which was treated with TFA by following the procedure described in Example 1 to afford the title compound.

M+1, +ESI=709

Example 32

N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide

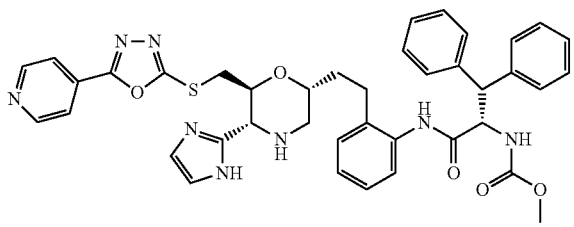 [SMILES: COC(=O)N[C@H](C(=O)Nc1ccccc1CC[C@@H]1CN[C@H](c2ncc[nH]2)[C@@H](CSc2nnc(-c3ccncc3)o2)O1)C(c1ccccc1)c1ccccc1]

Step 1: tert-butyl (2S,3S,6R)-3-formyl-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate To a stirred solution of oxalyl chloride (5 eq) in DCM (0.2 M) at −78° C. was added a solution of DMSO (10 eq) in DCM (0.2M). The reaction mixture was stirred at −78° C. for 30 min. A solution of tert-butyl (2S,3R,6R)-3-(hydroxymethyl)-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate (1 eq) in DCM (0.2 M) was added dropwise, stirred at −40° C. for 1.5 hours. The reaction mixture was then cooled to −78° C. and triethylamine (10 eq) was added and the mixture was stirred at 0° C. for 1 h. Water was added and the mixture was warmed to rt for 30 min. The mixture was poured into aqueous sodium hydrogen carbonate and the aqueous layer extracted with DCM. The combined organic layers were washed with brine, dried over MgSO₄, filtered and concentrated under vacuum to afford the title compound which was used in next step without further purification.

Step 2: N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide To tert-butyl (2S,3S,6R)-3-formyl-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate (1 eq) and glyoxal trimer dihydrate (0.5 eq) in MeOH (0.1M) was added 2 M AMMONIA (10 eq) in MeOH. The reaction mixture was stirred at 55° C. for 6 h. Upon cooling to rt, aqueous ammonium chloride was added, extracted with ethyl acetate. The combined organic layers were washed with brine, dried with MgSO₄ and concentrated under vacuum. The residue was purified by column chromatography on silica gel using automatized gradiant pump system CombiFlash eluting with ethyl acetate/hexanes (0:100 to 100:0), followed by 10% MeOH/EtOAc, then the material was purified by reverse HPLC to afford the title compound. HPLC conditions: Max-RP (21×50 mm), 35-75% CH₃CN/15 nM NH₄HCO₃, 25 mL/min, λ 254 nm to afford tert-butyl (2S,3R,6R)-3-(1H-imidazol-2-yl)-6-[2-(2-{[N-(methoxycarbonyl)-β-phenyl-L-phenylalanyl]amino}phenyl)ethyl]-2-({[5-(pyridin-4-yl)-1,3,4-oxadiazol-2-yl]sulfanyl}methyl)morpholine-4-carboxylate which was treated with TFA by following procedure described in Example 1.

M+1, +ESI=745

Example 33

N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide

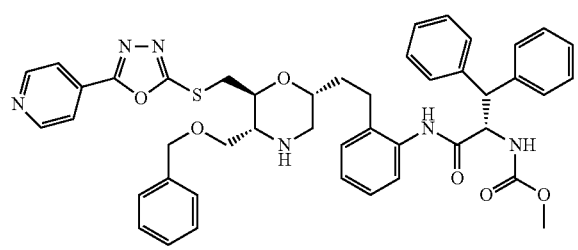 [SMILES: COC(=O)N[C@H](C(=O)Nc1ccccc1CC[C@@H]1CN[C@H](COCc2ccccc2)[C@@H](CSc2nnc(-c3ccncc3)o2)O1)C(c1ccccc1)c1ccccc1]

Step 1: tert-butyl (2S,3R,6R)-3-[(benzyloxy)methyl]-2-(hydroxymethyl)-6-[2-(2-{[N-(methoxycarbonyl)-β-phenyl-L-phenylalanyl]amino}phenyl)ethyl]morpholine-4-carboxylate To a stirred solution of tert-butyl (2S,3R,6R)-3-[(benzyloxy)methyl]-2-({[ten-butyl(diphenyl)silyl] oxy}methyl)-6-[2-(2-{[N-(methoxycarbonyl)-β-phenyl-L-phenylalanyl]amino}phenyl)ethyl]morpholine-4-carboxylate (1 eq) in THF (0.1M) at room temperature was added TBAF (1.5 eq). The reaction mixture was stirred at room temperature for 5 hours and was poured into water and the aqueous layer was extracted with ethyl acetate. The combined organic layers were washed with brine, dried with MgSO₄, filtered and concentrated under vacuum. The residue was purified by column chromatography on silica gel using automatized gradiant pump system CombiFlash eluting with ethyl acetate/hexanes (0:100 to 90:10) to give the title compound as a colorless foam.

Step 2: N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide was prepared from tert-butyl (2S,3R,6R)-3-[(benzyloxy)methyl]-2-(hydroxymethyl)-6-[2-(2-{[N-(methoxycarbonyl)-β-phenyl-L-phenylalanyl]amino}phenyl)ethyl]morpholine-4-carboxylate by following the procedures described in steps 12 and 13 of Example 30.

M+1, +ESI=799

Example 34

Nα-(methoxycarbonyl)-β-phenyl-N-(2-{2-[(2R,5R,6S)-6-({[5-(pyridin-4-yl)-1,3,4-oxadiazol-2-yl]sulfanyl}methyl)-5-({[(2,2,2-trifluoroethyl)carbamoyl]oxy}methyl)morpholin-2-yl]ethyl}phenyl)-L-phenylalaninamide

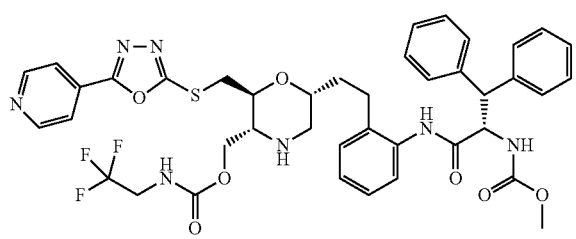 [SMILES: COC(=O)N[C@H](C(=O)Nc1ccccc1CC[C@@H]1CN[C@H](COC(=O)NCC(F)(F)F)[C@@H](CSc2nnc(-c3ccncc3)o2)O1)C(c1ccccc1)c1ccccc1]

Step 1: tert-butyl (2S,3R,6R)-2-({[tert-butyl(diphenyl)silyl]oxy}methyl)-6-[2-(2-{[N-(methoxycarbonyl)-β-phenyl-L-phenylalanyl]amino}phenyl)ethyl]-3-({[(2,2,2-trifluoroethyl)carbamoyl]oxy}methyl)morpholine-4-carboxylate To a stirred solution of tert-butyl (2S,3R,6R)-2-({[tert-butyl(diphenyl)silyl]oxy}methyl)-3-(hydroxymethyl)-6-[2-(2-{[N-(methoxycarbonyl)-β-phenyl-L-phenylalanyl]amino}phenyl)ethyl]morpholine-4-carboxylate (1 eq) in pyridine (0.1 M) at room temperature was added CDI (2.1 eq). The reaction mixture was stirred at room temperature for 6 h. 2,2,2-trifluoroethylamine (50 eq) was added, the reaction mixture was stirred at rt for 16 hrs and was concentrated to dryness. The residue was dissolved in EtOAc, the organic layer was washed with 5% of aq. KHSO₄, aqueous saturated sodium hydrogen carbonate, dried with MgSO₄, filtered and concentrated under vacuum. The residue was purified by column chromatography on silica gel using automatized gradiant pump system CombiFlash eluting with ethyl acetate/hexanes (0:100 to 50:50) to give the title compound as a colorless foam.

Step 2: Nα-(methoxycarbonyl)-β-phenyl-N-(2-{2-[(2R,5R,6S)-6-({[5-(pyridin-4-yl)-1,3,4-oxadiazol-2-yl]sulfanyl}methyl)-5-({[(2,2,2-trifluoroethyl)carbamoyl]oxy}methyl)morpholin-2-yl]ethyl}phenyl)-L-phenylalaninamide Nα-(methoxycarbonyl)-β-phenyl-N-(2-{2-[(2R,5R,6S)-6-({[5-(pyridin-4-yl)-1,3,4-oxadiazol-2-yl]sulfanyl}methyl)-5-({[(2,2,2-trifluoroethyl)carbamoyl]oxy}methyl)morpholin-2-yl]ethyl}phenyl)-L-phenylalaninamide was prepared from tert-butyl (2S,3R,6R)-2-({[tert-butyl(diphenyl)silyl]oxy}methyl)-6-[2-(2-{[N-(methoxycarbonyl)-β-phenyl-L-phenylalanyl]amino}phenyl)ethyl]-3-({[(2,2,2-trifluoroethyl)carbamoyl]oxy}methyl)morpholine-4-carboxylate by following the procedures described in steps 1 and 2 of Example 33.

M+1, +ESI=834.

Example 35

N-(2-{2-[(2R,5R,6S)-5-({[(4-fluorobenzyl)carbamoyl]oxy}methyl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide

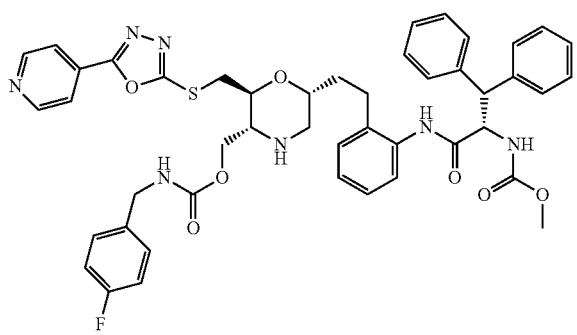 [SMILES: COC(=O)N[C@H](C(=O)Nc1ccccc1CC[C@@H]1CN[C@H](COC(=O)NCc2ccc(F)cc2)[C@@H](CSc2nnc(-c3ccncc3)o2)O1)C(c1ccccc1)c1ccccc1]

Step 1: N-(2-{2-[(2R,5R,6S)-5-({[(4-fluorobenzyl)carbamoyl]oxy}methyl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide N-(2-{2-[(2R,5R,6S)-5-({[(4-fluorobenzyl)carbamoyl]oxy}methyl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide was prepared from tert-butyl (2S,3R,6R)-2-({[tert-butyl(diphenyl)silyl]oxy}methyl)-3-(hydroxymethyl)-6-[2-(2-{[N-(methoxycarbonyl)-β-phenyl-L-phenylalanyl]amino}phenyl)ethyl]morpholine-4-carboxylate by following the procedures described in Example 34.

M+1, +ESI=860.

Example 36

N-[2-(2-{(2R,5R,6S)-5-[(carbamoyloxy)methyl]-6-methylmorpholin-2-yl}ethyl)-3-fluorophenyl]-4-fluoro-β-(4-fluorophenyl)-L-phenylalaninamide

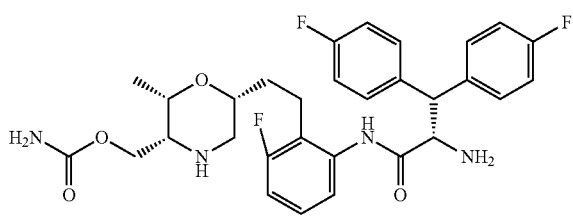 [SMILES: C[C@@H]1O[C@H](CCc2c(F)cccc2NC(=O)[C@@H](N)C(c2ccc(F)cc2)c2ccc(F)cc2)CN[C@@H]1COC(N)=O]

Step 1: (2S,3S)-methyl 2-(benzylamino)-3-hydroxybutanoate

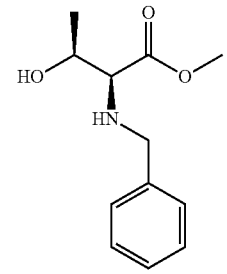 [SMILES: COC(=O)[C@@H](NCc1ccccc1)[C@H](C)O]

To a solution of (2S,3S)-methyl 2-amino-3-hydroxybutanoate (1 eq) in MeOH (1.5 M) at 0° C. was added triethylamine (1 eq). The reaction mixture was stirred for 10 minutes then benzaldehyde (1 eq) was added. The reaction mixture was stirred for 2 hours. NaBH$_4$ (1.5 eq) was added portionwise to the reaction mixture over 30 minutes. The reaction mixture was slowly added to a mixture of NH$_4$Cl (50 mL, sat. aq) and EtOAc (50 mL). The product was extracted 3× with EtOAc. The combined organic layers were washed with brine, dried over Na$_2$SO$_4$, filtered and concentrated to give the desired product as a white solid, which was used in the next step without purification. (84% yield; LC/MS: M+1=224.3, RT=0.82 min)

Step 2: (2R,3S)-2-benzylamino)butane-1,3-diol

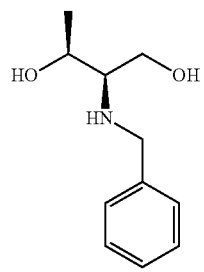

To (2S,3S)-methyl 2-(benzylamino)-3-hydroxybutanoate (1 eq) in THF (0.27 M) was added MeOH (2 eq) then LiBH$_4$ (2 eq, 2M in THF) slowly over 30 minutes. An ice bath was used to control the exotherm that occurred during the addition of the LiBH$_4$. The reaction was stirred at room temperature overnight then carefully and slowly quenched with NH$_4$Cl (sat. aq). The organic layer was extracted 1× with EtOAc, dried over Na$_2$SO$_4$, filtered and concentrated to give the desired product as a clear colorless gum which was used in the next step without purification. (99% yield; LC/MS: M+1=196.3, RT=0.55 min)

Step 3: (2S,3R)-3-(benzylamino)-4-((tert-butyldimethylsilyl)oxy)butan-2-ol

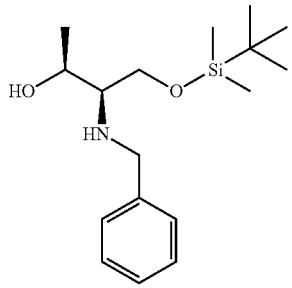 [SMILES: C[C@H](O)[C@@H](CO[Si](C)(C)C(C)(C)C)NCc1ccccc1]

To (2R,3S)-2-benzylamino)butane-1,3-diol (1 eq) in DCM (0.15 M) at 0° C. was added triethylamine (1.2 eq) and N,N-dimethylpyridin-4-amine (0.05 eq). Next, tert-butylchlorodimethylsilane (1 eq) in DCM (1.2 M) was added dropwise. The reaction was stirred at 0° C. for 2.5 hrs. The reaction was diluted with water. The organic layer was extracted 1× with DCM, washed 1× $NH_4Cl$ (sat. aq), dried over $Na_2SO_4$, filtered and concentrated. Purification on silica gel (120 g), eluting with a gradient of 0-10% MeOH/DCM afforded the title compound as a colorless oil. (21% yield; LC/MS: M+1=310.5, RT=1.80 min).

Step 4: ((2S,5R,6S)-4-benzyl-5-(((tert-butyldimethylsilyl)oxy)methyl)-6-methylmorpholin-2-yl)methanol

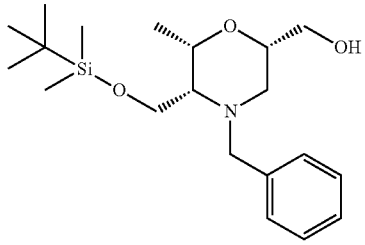 [SMILES: C[C@@H]1O[C@H](CO)CN(Cc2ccccc2)[C@@H]1CO[Si](C)(C)C(C)(C)C]

(2S,3R)-3-(benzylamino)-4-((tert-butyldimethylsilyl)oxy)butan-2-ol (1 eq) was dissolved in toluene and (R)-(−)-epichlorohydrin (1.3 eq) was added followed by the careful, slow, portionwise addition of lithium perchlorate (1.3 eq). The reaction was stirred at room temperature for 48 hours. MeOH (27 eq) was added to the reaction followed by the slow addition of sodium methoxide (2.5 eq). The reaction was stirred at room temperature for 48 hours. The reaction was quenched with $NH_4Cl$ (sat. aq.). The mixture was extracted 1× with EtOAc. The organic layer was washed 1× with brine, dried over $Na_2SO_4$, filtered and concentrated. Purification on silica gel (40 g), eluting with a gradient of 25-10% EtOAc/hexane afforded the title compound as a colorless oil. (67% yield; LC/MS: M+1=366.5, RT=2.05 min)

Step 5: (2S,3R,6S)-tert-butyl 3-(((tert-butyldimethylsilyl)oxy)methyl)-6-(hydroxymethyl)-2-methylmorpholine-4-carboxylate

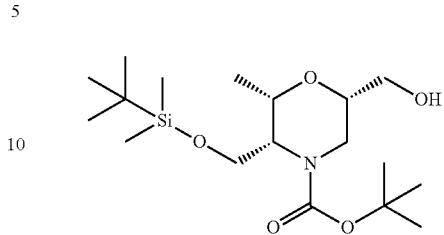

((2S,5R,6S)-4-benzyl-5-(((tert-butyldimethylsilyl)oxy)methyl)-6-methylmorpholin-2-yl)methanol (1 eq) was dissolved in ethanol in a Parr bottle. Nitrogen was bubbled through solution. Boc anhydride (1.2 eq), triethylamine (1 eq), and $Pd(OH)_2$ (0.2 eq) were added to the starting material. The reaction mixture was hydrogenated in the Parr at 45 psi overnight. The reaction was filtered through a small pad of celite to remove the palladium catalyst. The filtrate was concentrated to remove the ethanol. The residue was dissolved in EtOAc then washed 2× with water. The organic layer was dried over $Na_2SO_4$, filtered and concentrated to give the desired product as a colorless oil which was used in the next step without purification. (100% yield; LC/MS: M+1=376.5, loop)

Step 6: (2S,3R,6S)-tert-butyl 3-(((tert-butyldimethylsilyl)oxy)methyl)-6-formyl-2-methylmorpholine-4-carboxylate

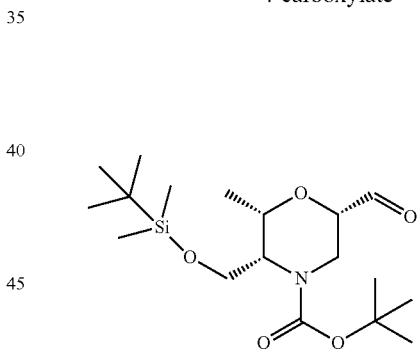

To a cooled solution of oxalyl chloride (2.0 eq) in anhydrous DCM (0.135 M) at −78° C. was added DMSO (2.2 eq) dropwise. After stirring for 10-15 minutes, a solution of (2S,3R,6S)-tert-butyl 3-(((tert-butyldimethylsilyl)oxy)methyl)-6-(hydroxymethyl)-2-methylmorpholine-4-carboxylate (1 eq) in DCM (0.62M) was added dropwise. Stirring was continued for another 15 minutes then diisopropylethylamine (9.0 eq) was added. Stirring was continued at −78° C. for two hours before the cold bath was removed. The reaction was stirred for 2 hours at room temperature. The reaction was carefully quenched with sodium hydrogen carbonate (sat. aq.) then extracted 2× with DCM. The combined organic layers were dried over $Na_2SO_4$, filtered and concentrated to give the desired product which was used in the next step without purification. (100% yield; LC/MS: M=373.6, loop)

Step 7: (2S,3R,6R)-tert-butyl 3-(((tert-butyldimethylsilyl)oxy)methyl)-6-((E)-2-fluoro-6-nitrostyryl)-2-methylmorpholine-4-carboxylate

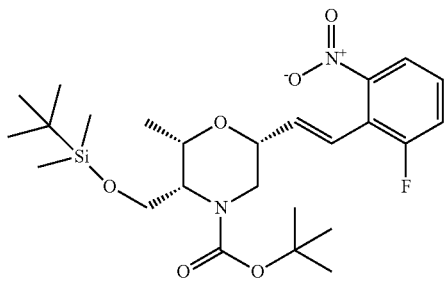

(2-fluoro-6-nitrobenzyl)(triphenylphosphonium bromide (1.1 eq), 18-Crown-6 (0.1 eq), and potassium carbonate (2.0 eq) were combined and stirred at room temperature for 5 minutes. (2S,3R,6S)-tert-butyl 3-(((tert-butyldimethylsilyl)oxy)methyl)-6-formyl-2-methylmorpholine-4-carboxylate (1 eq) in DME (0.133 M) was then added. The reaction mixture was stirred overnight at room temperature, filtered through celite and concentrated to dryness. Purification on silica gel (40 g), eluting with a gradient of 0-40% EtOAc/hexane afforded the title compound as a yellow gum/oil. (54% yield; LC/MS: M+1=511.5, RT=3.67 min)

Step 8: (2S,3R,6R)-tert-butyl 6-(2-amino-6-fluorophenethyl)-3-(((tert-butyldimethylsilyl)oxy)methyl)-2-methylmorpholine-4-carboxylate

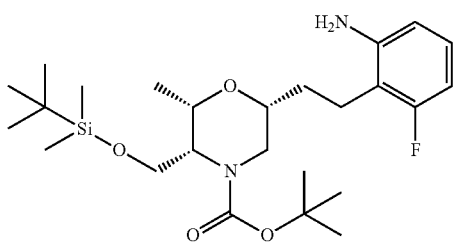 [SMILES: C[C@@H]1O[C@H](CCc2c(N)cccc2F)CN(C(=O)OC(C)(C)C)[C@@H]1CO[Si](C)(C)C(C)(C)C]

(2S,3R,6R)-tert-butyl 3-(((tert-butyldimethylsilyl)oxy)methyl)-6-((E)-2-fluoro-6-nitrostyryl)-2-methylmorpholine-4-carboxylate (1 eq) was dissolved in trifluoroethanol in a Parr bottle. Nitrogen was bubbled through the solution then Pd(OH)$_2$ (0.2 eq) was added. The mixture was hydrogenated in the Parr apparatus at 46 psi overnight. The mixture was filtered through celite to remove the catalyst then concentrated. The residue was dissolved in EtOAc, then washed 2× with water. The organic layer was dried over Na$_2$SO$_4$, filtered and concentrated to give the desired product which was used in the next step without purification. (88% yield; LC/MS: M+1=483.5, RT=1.34 min)

Step 9: (2S,3R,6R)-tert-butyl 6-(2-((S)-2-((tert-butoxycarbonyl)amino)-3,3-bis(4-fluorophenyl)propanamido)-6-fluorophenethyl)-3-(((tert-butyldimethylsilyl)oxy)methyl)-2-methylmorpholine-4-carboxylate

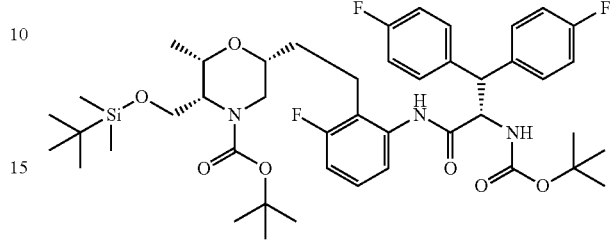

Phosphorus oxychloride (1.1 eq) was added to a solution of (2S,3R,6R)-tert-butyl 6-(2-amino-6-fluorophenethyl)-3-(((tert-butyldimethylsilyl)oxy)methyl)-2-methylmorpholine-4-carboxylate (1.0 eq) and (S)-2-((tert-butoxycarbonyl)amino)-3,3-bis(4-fluorophenyl)propanoic acid (1.0 eq) in anhydrous pyridine (0.16 M) at −15° C. and the reaction was stirred for thirty minutes. The reaction was allowed to warm to 0° C. and stirred for three hours. The reaction was quenched with KH$_2$PO$_4$ (sat. aq) and the mixture extracted 3× with EtOAc. The combined organic layers were dried over Na$_2$SO$_4$, filtered, and concentrated. Purification on silica gel (40 g), eluting with a gradient of 0-50% EtOAc/hexane afforded the title compound. (50% yield; LC/MS: M+1=842.7, RT=1.75 min)

Step 10: (2S,3R,6R)-tert-butyl 6-(2-((S)-2-((tert-butoxycarbonyl)amino)-3,3-bis(4-fluorophenyl)propanamido)-6-fluorophenethyl)-3-(hydroxymethyl)-2-methylmorpholine-4-carboxylate

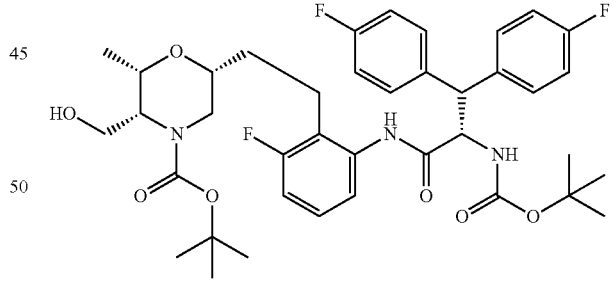

To a stirred solution of (2S,3R,6R)-tert-butyl 6-(2-((S)-2-((tert-butoxycarbonyl)amino)-3,3-bis(4-fluorophenyl)propanamido)-6-fluorophenethyl)-3-(((tert-butyldimethylsilyl)oxy)methyl)-2-methylmorpholine-4-carboxylate (1 eq) in THF (0.13 M) at room temperature was added TBAF (2 eq). The reaction mixture was stirred at room temperature for 5 hours. The reaction was quenched with KH$_2$PO$_4$ (sat. aq). The mixture was extracted 3× with EtOAc. The combined organic layers were dried over Na$_2$SO$_4$, filtered, and concentrated to give the desired product as a yellow solid which was used in the next step without purification. (100% yield; LC/MS: M+1=728.6, RT=2.85 min)

Step 11: (2S,3R,6R)-tert-butyl 6-(2-((S)-2-((tert-butoxycarbonyl)amino)-3,3-bis(4-fluorophenyl)propanamido)-6-fluorophenethyl)-3-((carbamoyloxy)methyl)-2-methylmorpholine-4-carboxylate

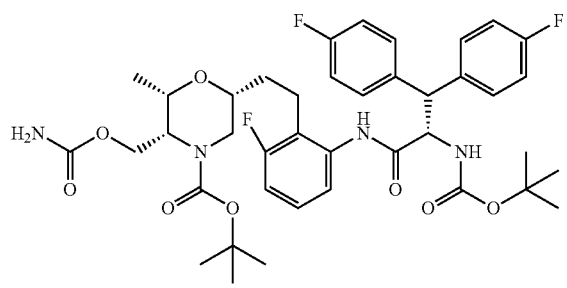 [SMILES: C[C@@H]1O[C@H](CCc2c(F)cccc2NC(=O)[C@@H](NC(=O)OC(C)(C)C)C(c2ccc(F)cc2)c2ccc(F)cc2)CN(C(=O)OC(C)(C)C)[C@@H]1COC(N)=O]

To a mixture of (2S,3R,6R)-tert-butyl 6-(2-((S)-2-((tert-butoxycarbonyl)amino)-3,3-bis(4-fluorophenyl)propanamido)-6-fluorophenethyl)-3-(hydroxymethyl)-2-methylmorpholine-4-carboxylate (1.0 eq) and N,N'-carboyldiimidazole (5.0 eq) in a microwave vial was added anhydrous pyridine (0.03 M). The microwave vial was sealed and the resulting solution was stirred at 60° C. for two hours then checked for the disappearance of the starting material and formation of the intermediate imidazolecarboxylate Ammonia gas (excess eq) was bubbled through the reaction mixture to saturate the solution. The microwave vial was recapped and the resulting mixture further stirred overnight at 60° C. The reaction was concentrated to remove the pyridine and the residue dissolved in ethyl acetate. The organic layer was washed 1× with 5% aq KHSO₄, then 1× sat. NaHCO₃, dried with Na₂SO₄, filtered, and concentrated. Purification on silica gel (4 g), eluting with a gradient of 25-100% EtOAc/hexane afforded the title compound. (42% yield; LC/MS: M+1=771.6, RT=2.81 min)

Step 12: (2S,3R,6R)-6-(2-((S)-2-amino-3,3-bis(4-fluorophenyl)propanamido)-6-fluorophenethyl)-2-methylmorpholine-3-yl)methyl carbamate

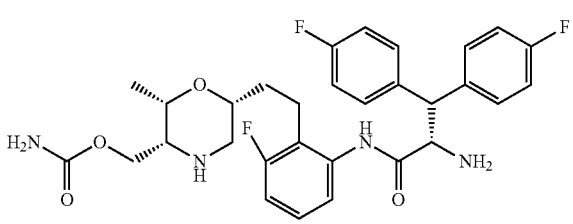 [SMILES: C[C@@H]1O[C@H](CCc2c(F)cccc2NC(=O)[C@@H](N)C(c2ccc(F)cc2)c2ccc(F)cc2)CN[C@@H]1COC(N)=O]

An excess of 4M HCl in dioxane was added to (2S,3R,6R)-tert-butyl 6-(2-((S)-2-((tert-butoxycarbonyl)amino)-3,3-bis(4-fluorophenyl)propanamido)-6-fluorophenethyl)-3-((carbamoyloxy)methyl)-2-methylmorpholine-4-carboxylate (1 eq). The reaction was stirred at room temperature for 30 minutes. The reaction was concentrated. Ether was added to the residue. The white suspension was stirred for 10 min. Filtration and washing with ether then afforded the desired product as an off-white solid. (85% yield; LC/MS: M+1=571.5, RT=1.49 min; >95% pure).

Example 37

4-fluoro-N-[3-fluoro-2-(2-{(2R,5R,6S)-6-methyl-5-[({[(1S)-2,2,2-trifluoro-1-methylethyl]carbamoyl}oxy)methyl]morpholin-2-yl}ethyl)phenyl]-β-(4-fluorophenyl)-L-phenylalaninamide

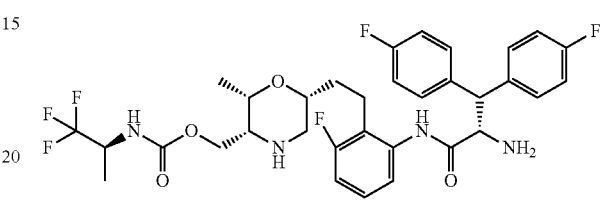

Step 1: ((2S,3R,6R)-tert-butyl 6-(2-((S)-2-((tert-butoxycarbonyl)amino)-3,3-bis(4-fluorophenyl)propanamido)-6-fluorophenethyl)-2-methyl-3-(((((S)-1,1,1-trifluoropropan-2-yl)carbamoyl)oxy)methyl)morpholine-4-carboxylate

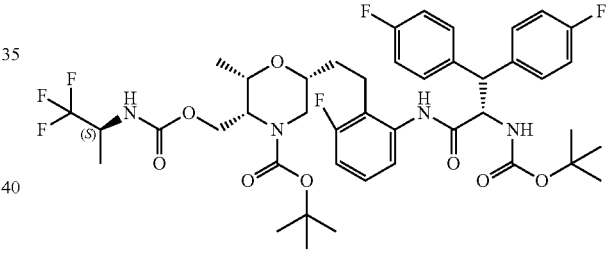

To a mixture of (2S,3R,6R)-tert-butyl 6-(2-((S)-2-((tert-butoxycarbonyl)amino)-3,3-bis(4-fluorophenyl)propanamido)-6-fluorophenethyl)-3-(hydroxymethyl)-2-methylmorpholine-4-carboxylate (1.0 eq) and N,N'-carboyldiimidazole (Example 36, step 10) (5.0 eq) was added anhydrous pyridine (0.03 M). The resulting solution was stirred at 60° C. overnight then checked for the disappearance of the starting material and formation of the intermediate imidazolecarboxylate. L-2,2,2-trifluoro-1-(methyl)ethylamine (10 eq) was added to the reaction mixture which was further stirred over the weekend at 60° C. A second batch of L-2,2,2-trifluoro-1-(methyl)ethylamine (10 eq) was added to the reaction mixture which was stirred overnight at 60° C. A third batch of L-2,2,2-trifluoro-1-(methyl)ethylamine (10 eq) was added to the reaction mixture which was stirred for two more days at 60° C. The reaction was concentrated to remove the pyridine. The residue was purified by preparative HPLC Reverse Phase (C-18), eluting with 15-95% Acetonitrile/Water+0.1% TFA to give the desired product as a white solid. (12% yield; LC/MS: M+1=867.7, RT=3.04 min).

Step 2: ((2S,3R,6R)-6-(2-((S)-2-amino-3,3-bis(4-fluorophenyl)propanamido)-6-fluorophenethyl)-2-methylmorpholin-3-yl)methyl ((S)-1,1-trifluoropropan-2-yl)carbamate

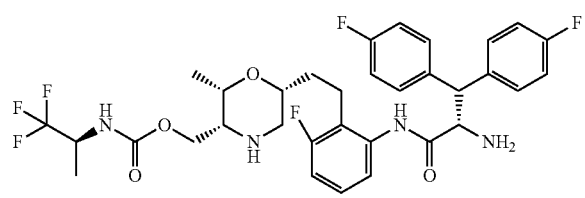 [SMILES: C[C@@H]1O[C@H](CCc2c(F)cccc2NC(=O)[C@@H](N)C(c2ccc(F)cc2)c2ccc(F)cc2)CN[C@@H]1COC(=O)N[C@@H](C)C(F)(F)F]

An excess of 4M HCl in dioxane was added to ((2S,3R,6R)-tert-butyl 6-(2-((S)-2-((tert-butoxycarbonyl)amino)-3,3-bis(4-fluorophenyl)propanamido)-6-fluorophenethyl)-2-methyl-3-(((((S)-1,1,1-trifluoropropan-2-yl)carbamoyl)oxy)methyl)morpholine-4-carboxylate (1 eq). The reaction was stirred at room temperature for 30 minutes. The reaction was concentrated. The residue was dissolved in MeOH and loaded onto a Porapak cartridge that had been conditioned with MeOH. The cartridge was washed with 2CV of MeOH and the eluent discarded. The desired product was then eluted with 2CV of 2M ammonia in MeOH. The filtrate was concentrated to afford the title compound as a white solid. (87% yield; LC/MS: M+1=667.5, RT=1.63 min; >90% pure)

Example 38

4-fluoro-N-[3-fluoro-2-(2-{(2R,5R,6S)-5-[({[(1R)-1-(4-fluorophenyl)propyl]carbamoyl}oxy)methyl]-6-methylmorpholin-2-yl}ethyl)phenyl]-β-(4-fluorophenyl)-L-phenylalaninamide

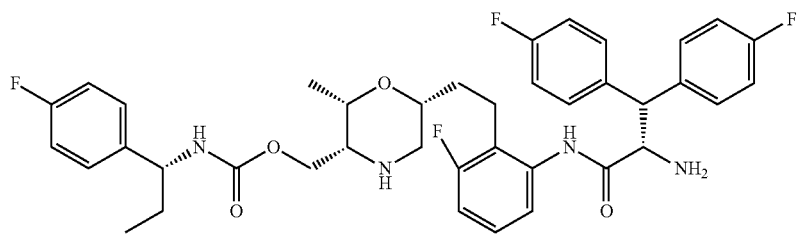 [SMILES: CC[C@@H](NC(=O)OC[C@H]1NC[C@@H](CCc2c(F)cccc2NC(=O)[C@@H](N)C(c2ccc(F)cc2)c2ccc(F)cc2)O[C@H]1C)c1ccc(F)cc1]

Step 1: ((2S,3R,6R)-tert-butyl 6-(2-((S)-2-((tert-butoxycarbonyl)amino)-3,3-bis(4-fluorophenyl)propanamido)-6-fluorophenethyl)-3-(((((R)-1-(4-fluorophenyl)propyl)carbamoyl)oxy)methyl)-2-methylmorpholine-4-carboxylate

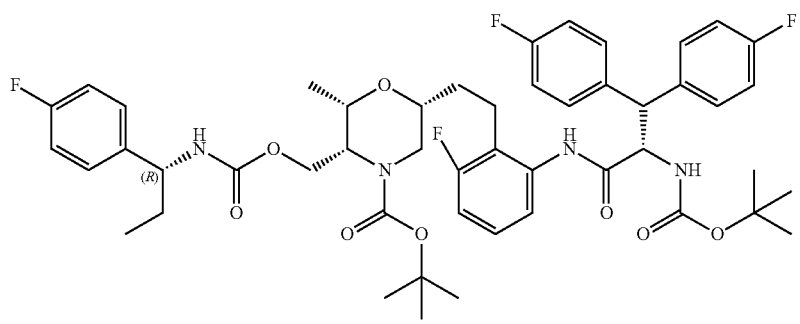

To a mixture of (2S,3R,6R)-tert-butyl 6-(2-((S)-2-((tert-butoxycarbonyl)amino)-3,3-bis(4-fluorophenyl)propanamido)-6-fluorophenethyl)-3-(hydroxymethyl)-2-methylmorpholine-4-carboxylate (1.0 eq) and N,N'-carboyldiimidazole (Example 36, step 10) (5.0 eq) was added anhydrous pyridine (0.03 M). The resulting solution was stirred at 60° C. overnight then checked for the disappearance of the starting material and formation of the intermediate imidazolecarboxylate. (R)-1-(4-fluorophenyl)propan-1-amine (10 eq) was added to the reaction mixture which was further stirred for several days at 60° C. The reaction was concentrated to remove the pyridine. The residue was purified by preparative HPLC Reverse Phase (C-18), eluting with 15-95% Acetonitrile/Water+0.1% TFA to give the desired product as a white solid. (31% yield; LC/MS: M-boc=807.7, RT=3.21 min)

Step 2: ((2S,3R,6R)-6-(2-((S)-2-amino-3,3-bis(4-fluorophenyl)propanamido)-6-fluorophenethyl)-2-methylmorpholin-3-yl)methyl ((R)-1-(4-fluorophenyl)propyl)carbamate

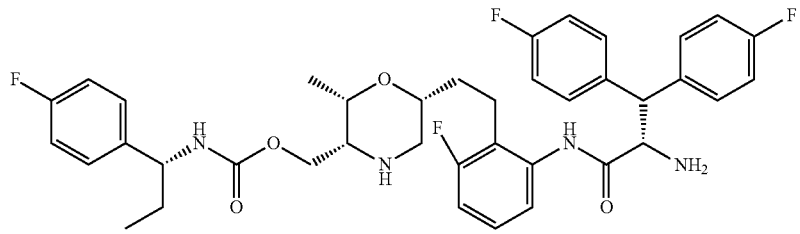 [SMILES: CC[C@@H](NC(=O)OC[C@H]1NC[C@@H](CCc2c(F)cccc2NC(=O)[C@@H](N)C(c2ccc(F)cc2)c2ccc(F)cc2)O[C@H]1C)c1ccc(F)cc1]

An excess of 4M HCl in dioxane was added to (2S,3R,6R)-tert-butyl 6-(2-((S)-2-((tert-butoxycarbonyl)amino)-3,3-bis(4-fluorophenyl)propanamido)-6-fluorophenethyl)-3-(hydroxymethyl)-2-methylmorpholine-4-carboxylate (1 eq). The reaction was stirred at room temperature for 45 minutes. The reaction was concentrated. The residue was dissolved in MeOH and loaded onto a Porapak cartridge that had been conditioned with MeOH. The cartridge was washed with 2CV of MeOH and the eluent discarded. The desired product was then eluted with with 2CV of 2M ammonia in MeOH. The filtrate was concentrated to afford the title compound as a beige solid. (84% yield; LC/MS: M+1=707.7, RT=1.81 min; >95% pure).

| Ex. | Structure | IUPAC Name | Exact Mass [M + H]+ |
|---|---|---|---|
| 39 | 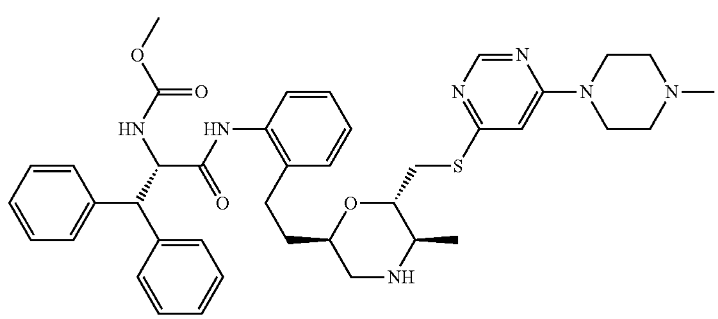 [SMILES: COC(=O)N[C@H](C(=O)Nc1ccccc1CC[C@@H]1CN[C@H](C)[C@@H](CSc2cc(N3CCN(C)CC3)ncn2)O1)C(c1ccccc1)c1ccccc1] | Nα-(methoxycarbonyl)-N-(2-{2-[(2R,5R,6S)-5-methyl-6-({[6-(4-methylpiperazin-1-yl)pyrimidin-4-yl]sulfanyl}methyl)morpholin-2-yl]ethyl}phenyl)-β-phenyl-L-phenylalaninamide | 724.4 |
| 40 | 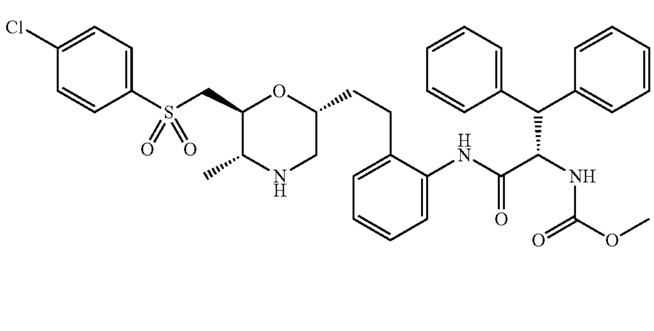 [SMILES: COC(=O)N[C@H](C(=O)Nc1ccccc1CC[C@@H]1CN[C@H](C)[C@@H](CS(=O)(=O)c2ccc(Cl)cc2)O1)C(c1ccccc1)c1ccccc1] | N-(2-{2-[(2R,5R,6S)-6-{[(4-chlorophenyl)sulfonyl]methyl}-5-methylmorpholin-2-yl]ethyl}phenyl)-Nα-(methoxycarbonyl)-β-phenyl-L-phenylalaninamide | 690.2 |

-continued

| Ex. | Structure | IUPAC Name | Exact Mass [M + H]+ |
|---|---|---|---|
| 41 | 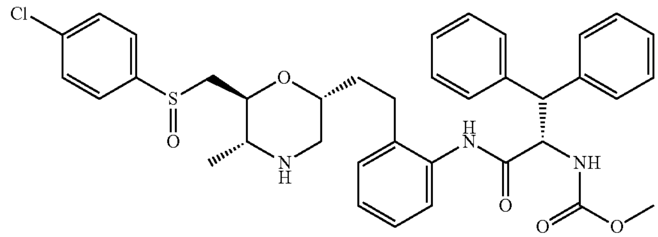 [SMILES: COC(=O)N[C@H](C(=O)Nc1ccccc1CC[C@@H]1CN[C@H](C)[C@@H](CS(=O)c2ccc(Cl)cc2)O1)C(c1ccccc1)c1ccccc1] | N-(2-{2-[(2R,5R,6S)-6-{[(R)-(4-chlorophenyl)sulfinyl]methyl}-5-methylmorpholin-2-yl]ethyl}phenyl)-Nα-(methoxycarbonyl)-β-phenyl-L-phenylalaninamide | 674.2 |
| 42 | 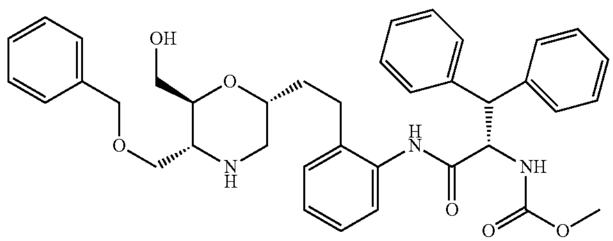 [SMILES: COC(=O)N[C@H](C(=O)Nc1ccccc1CC[C@@H]1CN[C@H](COCc2ccccc2)[C@@H](CO)O1)C(c1ccccc1)c1ccccc1] | N-(2-{2-[(2R,5R,6S)-5-[(benzyloxy)methyl]-6-(hydroxymethyl)morpholin-2-yl]ethyl}phenyl)-Nα-(methoxycarbonyl)-β-phenyl-L-phenylalaninamide | 638.3 |
| 43 | 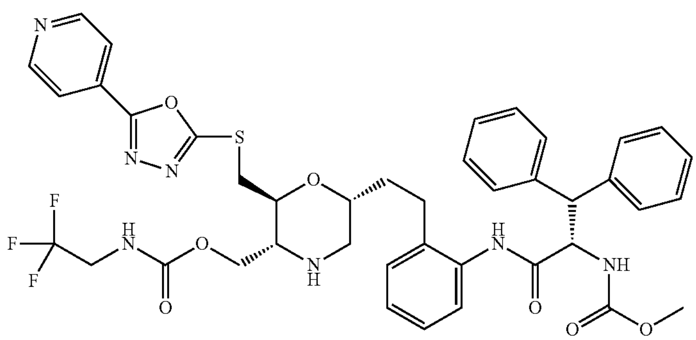 [SMILES: COC(=O)N[C@H](C(=O)Nc1ccccc1CC[C@@H]1CN[C@H](COC(=O)NCC(F)(F)F)[C@@H](CSc2nnc(-c3ccncc3)o2)O1)C(c1ccccc1)c1ccccc1] | Nα-(methoxycarbonyl)-β-phenyl-N-(2-{2-[(2R,5R,6S)-6-{[(5-pyridin-4-yl-1,3,4-oxadiazol-2-yl)sulfanyl]methyl}-5-({[(2,2,2-trifluoroethyl)carbamoyl]oxy}methyl)morpholin-2-yl]ethyl}phenyl)-L-phenylalaninamide | 834.3 |
| 44 | 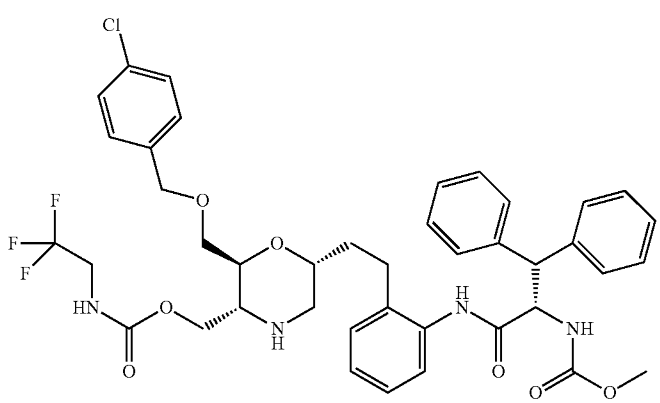 [SMILES: COC(=O)N[C@H](C(=O)Nc1ccccc1CC[C@@H]1CN[C@H](COC(=O)NCC(F)(F)F)[C@@H](COCc2ccc(Cl)cc2)O1)C(c1ccccc1)c1ccccc1] | N-(2-{2-[(2R,5R,6S)-6-{[(4-chlorobenzyl)oxy]methyl}-5-({[(2,2,2-trifluoroethyl)carbamoyl]oxy}methyl)morpholin-2-yl]ethyl}phenyl)-Nα-(methoxycarbonyl)-β-phenyl-L-phenylalaninamide | 797.3 |

-continued

| Ex. | Structure | IUPAC Name | Exact Mass [M + H]+ |
|---|---|---|---|
| 45 | 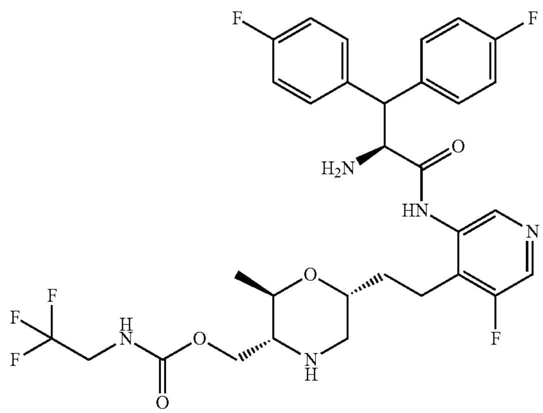 [SMILES: C[C@H]1O[C@H](CCc2c(F)cncc2NC(=O)[C@@H](N)C(c2ccc(F)cc2)c2ccc(F)cc2)CN[C@@H]1COC(=O)NCC(F)(F)F] | 4-fluoro-N-(5-fluoro-4-{2-[(2R,5R,6R)-6-methyl-5-({[(2,2,2-trifluoroethyl)carbamoyl]oxy}methyl)morpholin-2-yl]ethyl}pyridin-3-yl)-β-(4-fluorophenyl)-L-phenylalaninamide | 654.3 |
| 46 | 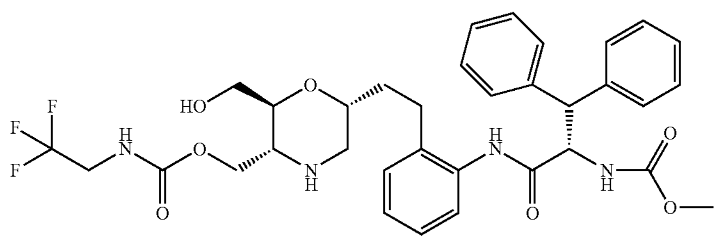 [SMILES: COC(=O)N[C@H](C(=O)Nc1ccccc1CC[C@@H]1CN[C@H](COC(=O)NCC(F)(F)F)[C@@H](CO)O1)C(c1ccccc1)c1ccccc1] | N-(2-{2-[(2R,5R,6S)-6-(hydroxymethyl)-5-({[(2,2,2-trifluoroethyl)carbamoyl]oxy}methyl)morpholin-2-yl]ethyl}phenyl)-Nα-(methoxycarbonyl)-β-phenyl-L-phenylalaninamide | 673.3 |
| 47 | 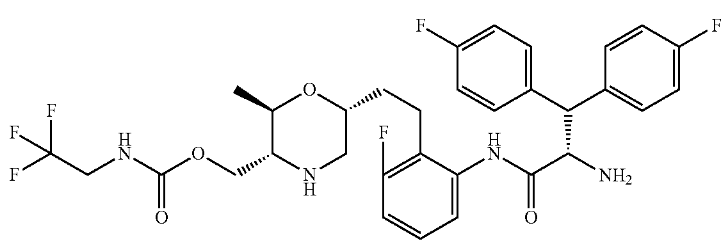 [SMILES: C[C@H]1O[C@H](CCc2c(F)cccc2NC(=O)[C@@H](N)C(c2ccc(F)cc2)c2ccc(F)cc2)CN[C@@H]1COC(=O)NCC(F)(F)F] | 4-fluoro-N-(3-fluoro-2-{2-[(2R,5R,6R)-6-methyl-5-({[(2,2,2-trifluoroethyl)carbamoyl]oxy}methyl)morpholin-2-yl]ethyl}phenyl)-β-(4-fluorophenyl)-L-phenylalaninamide | 653.3 |
| 48 | 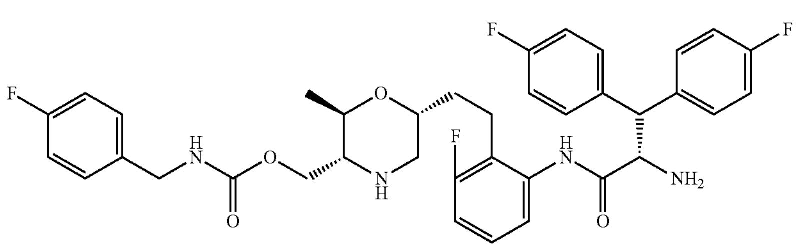 [SMILES: C[C@H]1O[C@H](CCc2c(F)cccc2NC(=O)[C@@H](N)C(c2ccc(F)cc2)c2ccc(F)cc2)CN[C@@H]1COC(=O)NCc1ccc(F)cc1] | 4-fluoro-N-(3-fluoro-2-{2-[(2R,5R,6R)-5-({[(4-fluorobenzyl)carbamoyl]oxy}methyl)-6-methylmorpholin-2-yl]ethyl}phenyl)-β-(4-fluorophenyl)-L-phenylalaninamide | 679.3 |
| 49 | 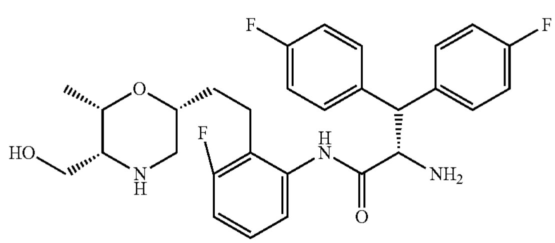 [SMILES: C[C@@H]1O[C@H](CCc2c(F)cccc2NC(=O)[C@@H](N)C(c2ccc(F)cc2)c2ccc(F)cc2)CN[C@@H]1CO] | 4-fluoro-N-(3-fluoro-2-{2-[(2R,5R,6S)-5-(hydroxymethyl)-6-methylmorpholin-2-yl]ethyl}phenyl)-β-(4-fluorophenyl)-L-phenylalaninamide | 528.2 |

| Ex. | Structure | IUPAC Name | Exact Mass [M + H]+ |
|---|---|---|---|
| 50 | 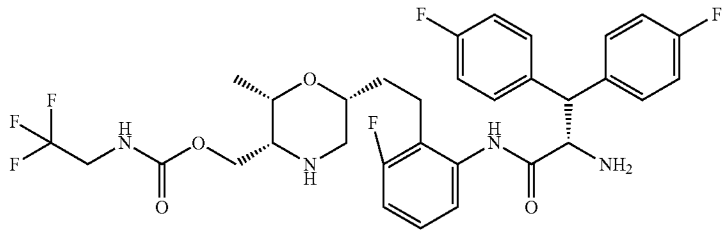 [SMILES: C[C@@H]1O[C@H](CCc2c(F)cccc2NC(=O)[C@@H](N)C(c2ccc(F)cc2)c2ccc(F)cc2)CN[C@@H]1COC(=O)NCC(F)(F)F] | 4-fluoro-N-(3-fluoro-2-{2-[(2R,5R,6S)-6-methyl-5-({[(2,2,2-trifluoroethyl)carbamoyl]oxy}methyl)morpholin-2-yl]ethyl}phenyl)-β-(4-fluorophenyl)-L-phenylalaninamide | 653.3 |
| 51 | 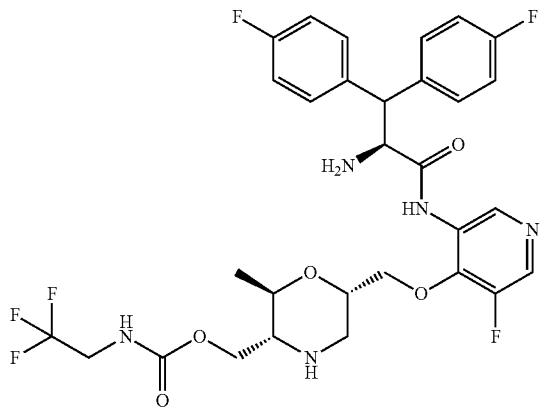 [SMILES: C[C@H]1O[C@H](COc2c(F)cncc2NC(=O)[C@@H](N)C(c2ccc(F)cc2)c2ccc(F)cc2)CN[C@@H]1COC(=O)NCC(F)(F)F] | 4-fluoro-N-(5-fluoro-4-{[(2S,5R,6R)-6-methyl-5-({[(2,2,2-trifluoroethyl)carbamoyl]oxy}methyl)morpholin-2-yl]methoxy}pyridin-3-yl)-β-(4-fluorophenyl)-L-phenylalaninamide | 656.2 |
| 52 | 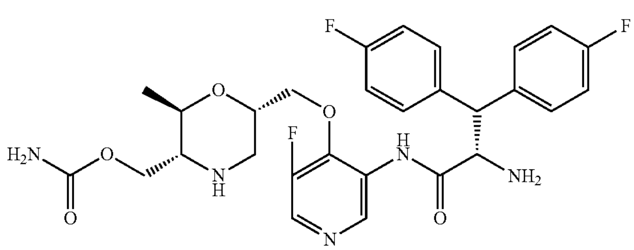 [SMILES: C[C@H]1O[C@H](COc2c(F)cncc2NC(=O)[C@@H](N)C(c2ccc(F)cc2)c2ccc(F)cc2)CN[C@@H]1COC(N)=O] | N-[4-({(2S,5R,6R)-5-[(carbamoyloxy)methyl]-6-methylmorpholin-2-yl}methoxy)-5-fluoropyridin-3-yl]-4-fluoro-β-(4-fluorophenyl)-L-phenylalaninamide | 574.2 |
| 53 | 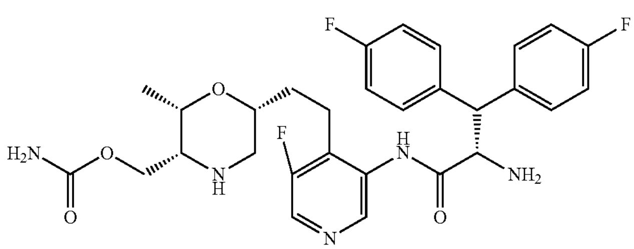 [SMILES: C[C@@H]1O[C@H](CCc2c(F)cncc2NC(=O)[C@@H](N)C(c2ccc(F)cc2)c2ccc(F)cc2)CN[C@@H]1COC(N)=O] | N-[4-(2-{(2R,5R,6S)-5-[(carbamoyloxy)methyl]-6-methylmorpholin-2-yl}ethyl)-5-fluoropyridin-3-yl]-4-fluoro-β-(4-fluorophenyl)-L-phenylalaninamide | 572.2 |
| 54 | 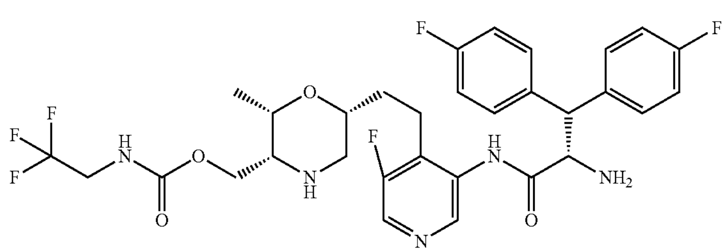 [SMILES: C[C@@H]1O[C@H](CCc2c(F)cncc2NC(=O)[C@@H](N)C(c2ccc(F)cc2)c2ccc(F)cc2)CN[C@@H]1COC(=O)NCC(F)(F)F] | 4-fluoro-N-(5-fluoro-4-{2-[(2R,5R,6S)-6-methyl-5-({[(2,2,2-trifluoroethyl)carbamoyl]oxy}methyl)morpholin-2-yl]ethyl}pyridin-3-yl)-β-(4-fluorophenyl)-L-phenylalaninamide | 654.3 |

| Ex. | Structure | IUPAC Name | Exact Mass [M + H]+ |
|---|---|---|---|
| 55 | 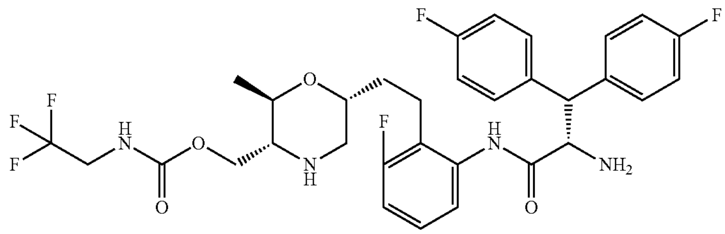 [SMILES: C[C@H]1O[C@H](CCc2c(F)cccc2NC(=O)[C@@H](N)C(c2ccc(F)cc2)c2ccc(F)cc2)CN[C@@H]1COC(=O)NCC(F)(F)F] | 4-fluoro-N-(3-fluoro-2-{2-[(2R,5R,6R)-6-methyl-5-({[(2,2,2-trifluoroethyl)carbamoyl]oxy}methyl)morpholin-2-yl]ethyl}phenyl)-β-(4-fluorophenyl)-L-phenylalaninamide | 653.3 |
| 56 | 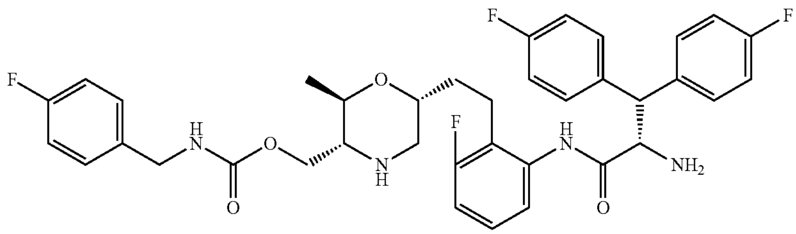 [SMILES: C[C@H]1O[C@H](CCc2c(F)cccc2NC(=O)[C@@H](N)C(c2ccc(F)cc2)c2ccc(F)cc2)CN[C@@H]1COC(=O)NCc1ccc(F)cc1] | 4-fluoro-N-(3-fluoro-2-{2-[(2R,5R,6R)-5-({[(4-fluorobenzyl)carbamoyl]oxy}methyl)-6-methylmorpholin-2-yl]ethyl}phenyl)-β-(4-fluorophenyl)-L-phenylalaninamide | 679.3 |
| 57 | 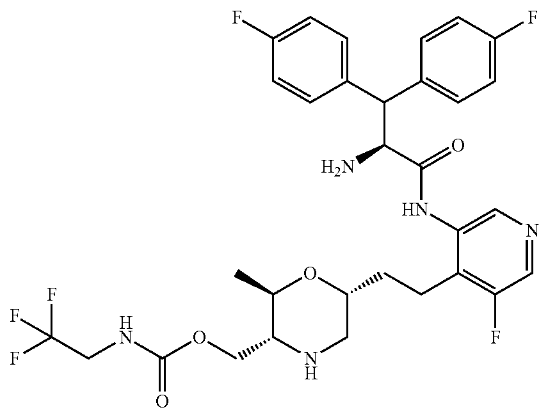 | 4-fluoro-N-(5-fluoro-4-{2-[(2R,5R,6R)-6-methyl-5-({[(2,2,2-trifluoroethyl)carbamoyl]oxy}methyl)morpholin-2-yl]ethyl}pyridin-3-yl)-β-(4-fluorophenyl)-L-phenylalaninamide | 654.3 |
| 58 | 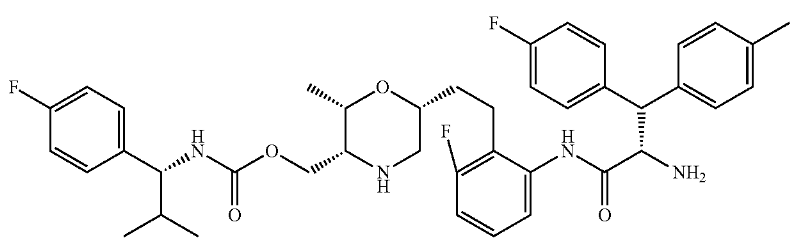 [SMILES: Cc1ccc(C(c2ccc(F)cc2)[C@H](N)C(=O)Nc2cccc(F)c2CC[C@@H]2CN[C@H](COC(=O)N[C@@H](c3ccc(F)cc3)C(C)C)[C@H](C)O2)cc1] | 4-fluoro-N-[3-fluoro-2-(2-{(2R,5R,6S)-5-[({[(1R)-1-(4-fluorophenyl)-2-methylpropyl]carbamoyl}oxy)methyl]-6-methylmorpholin-2-yl}ethyl)phenyl]-β-(4-fluorophenyl)-L-phenylalaninamide | 721.3 |
| 59 | 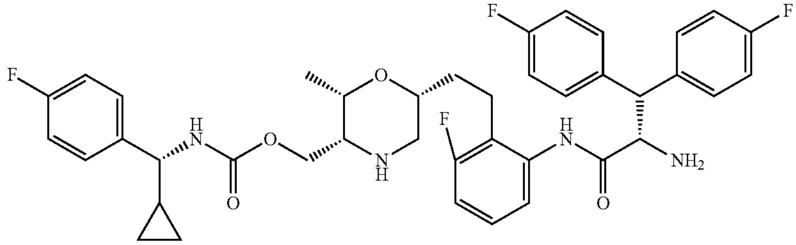 [SMILES: C[C@@H]1O[C@H](CCc2c(F)cccc2NC(=O)[C@@H](N)C(c2ccc(F)cc2)c2ccc(F)cc2)CN[C@@H]1COC(=O)N[C@@H](c1ccc(F)cc1)C1CC1] | N-[2-(2-{(2R,5R,6S)-5-[({[(R)-cyclopropyl(4-fluorophenyl)methyl]carbamoyl}oxy)methyl]-6-methylmorpholin-2-yl}ethyl)-3-fluorophenyl]-4-fluoro-β-(4-fluorophenyl)-L-phenylalaninamide | 719.3 |

| Ex. | Structure | IUPAC Name | Exact Mass [M + H]+ |
|---|---|---|---|
| 60 | 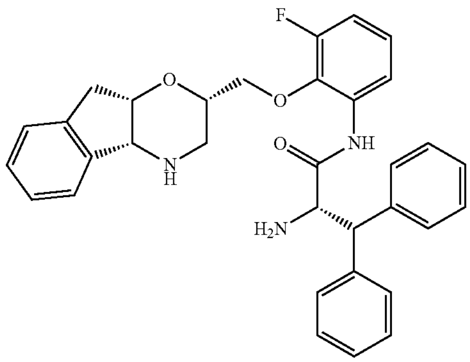 [SMILES: N[C@H](C(=O)Nc1cccc(F)c1OC[C@@H]1CN[C@@H]2c3ccccc3C[C@@H]2O1)C(c1ccccc1)c1ccccc1] | N-{3-fluoro-2-[(2S,4aR,9aS)-2,3,4,4a,9,9a-hexahydroindeno[2,1-b][1,4]oxazin-2-ylmethoxy]phenyl}-β-phenyl-L-phenylalaninamide | 538.3 |
| 61 | 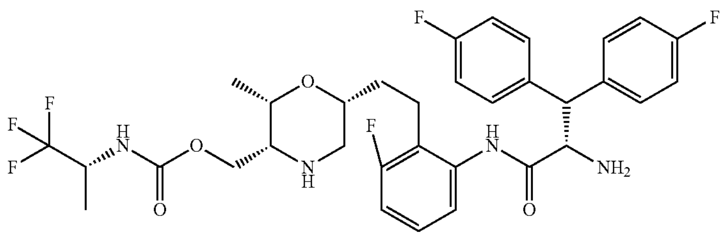 [SMILES: C[C@@H]1O[C@H](CCc2c(F)cccc2NC(=O)[C@@H](N)C(c2ccc(F)cc2)c2ccc(F)cc2)CN[C@@H]1COC(=O)N[C@H](C)C(F)(F)F] | 4-fluoro-N-[3-fluoro-2-(2-{(2R,5R,6S)-6-methyl-5-[({[(1R)-2,2,2-trifluoro-1-methylethyl]carbamoyl}oxy)methyl]morpholin-2-yl}ethyl)phenyl]-β-(4-fluorophenyl)-L-phenylalaninamide | 667.3 |
| 62 | 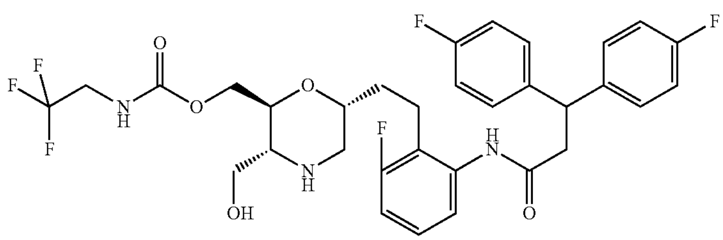 [SMILES: O=C(CC(c1ccc(F)cc1)c1ccc(F)cc1)Nc1cccc(F)c1CC[C@@H]1CN[C@H](CO)[C@@H](COC(=O)NCC(F)(F)F)O1] | [(2S,3R,6R)-6-[2-(2-{[3,3-bis(4-fluorophenyl)propanoyl]amino}-6-fluorophenyl)ethyl]-3-(hydroxymethyl)morpholin-2-yl]methyl(2,2,2-trifluoroethyl)carbamate | 654.2 |
| 63 | 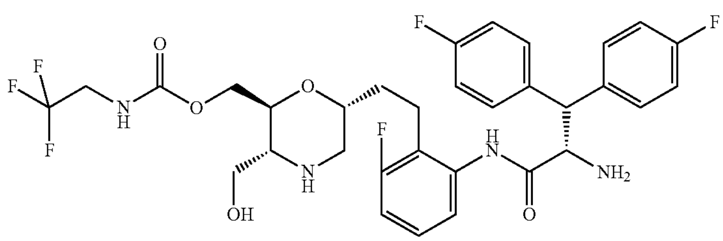 [SMILES: N[C@H](C(=O)Nc1cccc(F)c1CC[C@@H]1CN[C@H](CO)[C@@H](COC(=O)NCC(F)(F)F)O1)C(c1ccc(F)cc1)c1ccc(F)cc1] | 4-fluoro-N-(3-fluoro-2-{2-[(2R,5R,6S)-5-(hydroxymethyl)-6-({[(2,2,2-trifluoroethyl)carbamoyl]oxy}methyl)morpholin-2-yl]ethyl}phenyl)-β-(4-fluorophenyl)-L-phenylalaninamide | 669.3 |
| 64 | 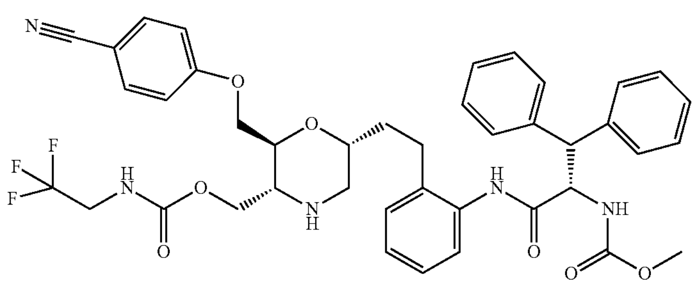 [SMILES: COC(=O)N[C@H](C(=O)Nc1ccccc1CC[C@@H]1CN[C@H](COC(=O)NCC(F)(F)F)[C@@H](COc2ccc(C#N)cc2)O1)C(c1ccccc1)c1ccccc1] | N-(2-{2-[(2R,5R,6S)-6-[(4-cyanophenoxy)methyl]-5-({[(2,2,2-trifluoroethyl)carbamoyl]oxy}methyl)morpholin-2-yl]ethyl}phenyl)-Nα-(methoxycarbonyl)-β-phenyl-L-phenylalaninamide | 774.3 |

Assay for Inhibition of Microbial Expressed HIV Protease ("Pepcleav")

Studies of the inhibition of the wildtype HIV-1 protease (which was expressed in *Escherichia coli*) were carried out with a peptide substrate [Val-Ser-Gln-Asn-(βnaphthyl)Ala-Pro-Ile-Val (SEQ ID NO:1)]. The inhibitor was first preincubated with the HIV-1 protease (wild type) enzyme in assay buffer (50 mM sodium acetate, pH 5.5, 100 mM NaCl, and 0.1% BSA) for 30 minutes at room temperature. Substrate was added to 400 micromolar in a total volume of 20 microliters containing 20 picomolar HIV-1 protease (final) and the reaction was incubated for 1 hour at 30° C. The reaction was quenched with the addition of formic acid and indinavir to 0.012% and 150 nM final concentrations, respectively. The product formation was determined after separation of product and substrate on a Zorbax Eclipse XDB-C18 column connected to an API 4000 mass spectrometer (Applied Biosystems) with multiple reaction monitoring (transitions were 644.5/428.9 and 615.4/422.2 (M1/M3) for product and indinavir respectively). The extent of inhibition of the reaction was determined from the peak area of the products. Analysis of the products, independently synthesized, provided quantitation standards and confirmation of the product composition. Compounds in the Examples of the present invention exhibited inhibition of HIV-1 protease in this assay as noted below in Table 1.

Antiviral Assays in Cell Culture ("Spread")

Acute Infection Assay ("Spread") data were generated using HIV-1 (H9IIIB strain) infection of MT-4 human T-lymphoid cells in 10% FBS, and according to the methods disclosed by J. P. Vacca et al, "L-735,524: An orally bioavailable human immunodeficiency virus type 1 protease inhibitor," Proc. Natl. Acad. Sci. USA, Vol. 91, pp. 4096-4100 (April 1994).

Data Table 1 displays data regarding Pepcleave and Spread data for each of the example compounds. Both columns of data in the table reflect the mean of at least two independent experiments

DATA TABLE 1

| Example | PEPCLEAV (nM) |
|---------|---------------|
| 1 | 17.51 |
| 2 | 222.3 |
| 3 | 7.521 |
| 4 | 10.61 |
| 5 | 4.959 |
| 6 | 5.124 |
| 7 | 7.951 |
| 8 | 8.353 |
| 9 | 8.485 |
| 10 | 9.433 |
| 11 | 11.71 |
| 12 | 11.85 |
| 13 | 12.5 |
| 14 | 14.21 |
| 15 | 17.75 |
| 16 | 21.54 |
| 17 | 25.1 |
| 18 | 34.93 |
| 19 | 41.41 |
| 20 | 43.26 |
| 21 | 44.3 |
| 22 | 44.44 |
| 23 | 51.91 |
| 24 | 58.27 |
| 25 | 100 |
| 26 | 124.3 |
| 27 | 124.5 |
| 28 | 214 |
| 29 | 235.5 |
| 30 | 0.03343 |
| 31 | 0.1705 |
| 32 | 0.6505 |
| 33 | 0.4717 |
| 34 | ND |
| 35 | 0.03035 |
| 36 | 39 |
| 37 | 3.1 |
| 38 | 4.4 |
| 39 | 420 |
| 40 | 750 |
| 41 | 890 |
| 42 | 80 |
| 43 | 0.01 |
| 44 | ND |
| 45 | 24 |
| 46 | 65 |
| 47 | 11 |

DATA TABLE 1-continued

| Example | PEPCLEAV (nM) |
|---------|---------------|
| 48 | 5.8 |
| 49 | 400 |
| 50 | 30 |
| 51 | 77 |
| 52 | 52 |
| 53 | 25 |
| 54 | 30 |
| 55 | 37 |
| 56 | 7.0 |
| 57 | 59 |
| 58 | 6.9 |
| 59 | 17 |
| 60 | 610 |
| 61 | 27 |
| 62 | 170 |
| 63 | 130 |
| 64 | ND |

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A compound of Formula I:

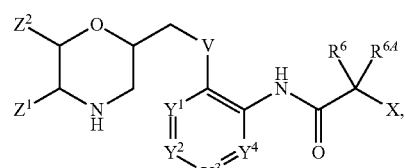

or a pharmaceutically acceptable salt thereof, wherein:

V is $CH_2$ or O;

$Y^1$, $Y^2$, $Y^3$ and $Y^4$ are independently selected from C(R) and N;

each X is independently selected from H and $NR^7R^8$;

$Z^1$ and $Z^2$ are independently selected from the group consisting of

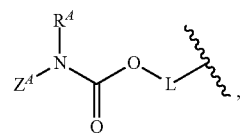

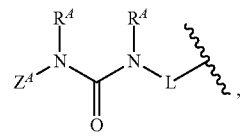

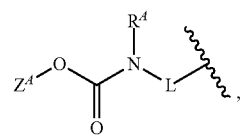

-continued

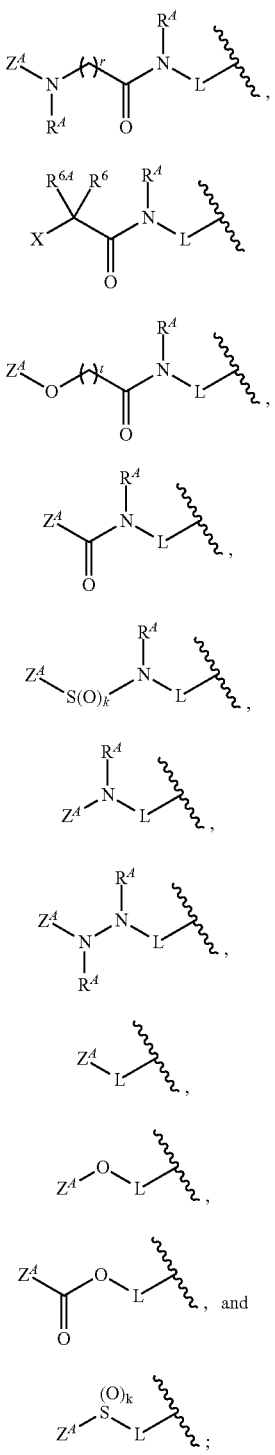

(4), (5), (6), (7), (8), (9), (10), (11), (12), (13), and (14)

or $Z^1$ and $Z^2$ may be joined together with the atoms to which they are attached to form HetB;

L is a linker selected from
(a) a bond,
(b) —$CH_2$—,
(c) —C(O)—,
(d) —$CH_2$—C(O)- or —C(O)—$CH_2$-,
(e) —$CH_2$—$CH_2$—C(O)- or —C(O)—$CH_2$—$CH_2$-, and

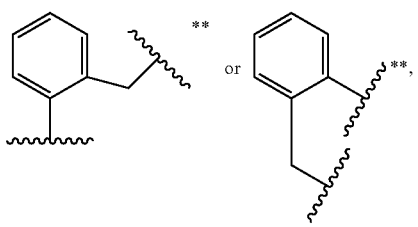

wherein ** shows the point of attachment to the morpholine;

R is selected from H, halo, hydroxy, $C_{1-4}$alkyl, $C_{1-4}$alkoxy, $C_{1-4}$alkyl-S(O)$_k$—, $CF_3$, CN, benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, $C_{1-4}$alkyl, $C_{1-4}$alkoxy, $CF_3$ and CN;

each k is independently 0, 1 or 2;
each r and t are independently 1, 2, 3 or 4;
$Z^A$ is selected from the group consisting of:
(1) hydrogen,
(2) $C_{1-10}$ alkyl,
(3) $C_{2-10}$alkenyl,
(4) $C_{3-7}$ cycloalkyl,
(5) AryA,
(6) HetA, and
(7) HetB, wherein said $C_{1-10}$ alkyl, $C_{2-10}$alkenyl and $C_{3-7}$ cycloalky are optionally substituted with 1 to 6 substituents as allowed by valence independently selected from the group consisting of: fluoro, hydroxy, carbamoyl, $C_{3-6}$ cycloalkyl, C(O)O—$C_{1-6}$ alkyl, C(O)OH, C(O)—$C_{1-6}$ alkyl, N(H)—$C_{1-6}$ alkyl, N(—$C_{1-6}$ alkyl)$_2$, ArylA, HetA and HetB;

each $R^A$ is independently H or $C_{1-6}$ alkyl;
or $Z^A$ and $R^A$ and the nitrogen atom to which they are attached may be joined together to form a 5-, 6- or 7-membered mono-cyclic, or 9- or 10-membered bi-cyclic, saturated, aromatic or partially aromatic ring, said ring optionally containing 1 to 3 additional heteroatoms selected from O, S and N, and said ring optionally substituted with from 1 to 3 of $X^A$;

$R^6$ is selected from:

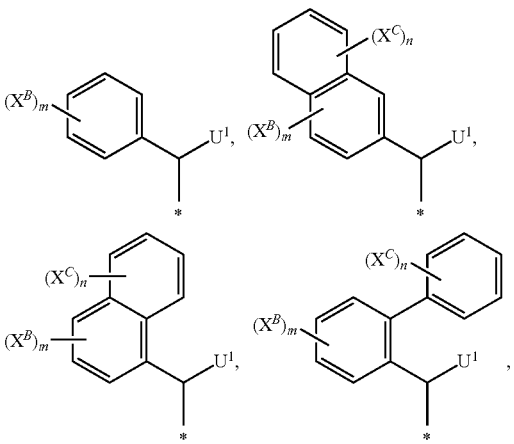

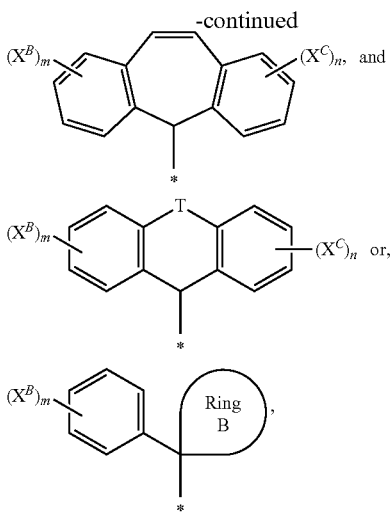

wherein the asterisk (*) denotes the point of attachment to the rest of the compound and $U^1$ is selected from (1) H, (2) $C_{1-10}$alkyl, wherein said $C_{1-10}$alkyl is optionally substituted with 1 to 4 substituents independently selected from halogen, $C_{1-4}$alkyl, $C_{1-4}$haloalkyl, hydroxy and $C_{1-4}$alkoxy, (3) $C_{3-7}$ cycloalkyl, wherein said $C_{3-7}$ cycloalkyl is optionally substituted with 1 to 4 substituents independently selected from halogen, $C_{1-4}$alkyl, $C_{1-4}$haloalkyl, hydroxy and $C_{1-4}$alkoxy, (4) ArylA, (5) HetA, (6) HetB, (7) $C_{1-10}$alkyl substituted with ArylA, (8) $C_{1-10}$alkyl substituted with HetA, and (9) $C_{1-10}$alkyl substituted with HetB; and Ring B is selected from $C_{3-7}$ cycloalky and HetB, wherein $C_{3-7}$ cycloalkyl is optionally substituted with 1 to 4 substituents independently selected from halogen, OH, $C_{1-4}$alkyl, $C_{1-4}$fluoroalkyl and $C_{1-4}$alkoxy;

each $R^{6A}$ independently is H or $C_{1-6}$ alkyl;

alternatively, $R^6$ and $R^{6A}$ together with the carbon to which they are attached form a $C_{3-6}$ cycloalkyl which is optionally substituted with phenyl, wherein the phenyl is optionally substituted with from 1 to 3 of $X^D$;

each $X^A$, each $X^B$, each $X^C$, each $X^D$, each $Y^B$ and each $Y^C$ are independently selected from the group consisting of:

(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) NO$_2$,
(15) NH$_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) C(O)NH$_2$,
(25) C(O)N(H)—$C_{1-6}$ alkyl,
(26) C(O)N(—$C_{1-6}$ alkyl)$_2$,
(27) C(O)N(H)C(O)—$C_{1-6}$ alkyl,
(28) C(O)N(H)CH(O)
(29) SO$_2$H,
(30) SO$_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or —CH$_2$—HetA, optionally substituted with 1 to 5 substituents selected from halogen and $C_{1-6}$ alkyl,
(33) trimethylsilyl, and
(34) $C_{2-6}$alkenyl, wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:

(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) NO$_2$,
(k) NH$_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) SO$_2$—$C_{1-6}$ alkyl;

T is O, S, S(O), or SO$_2$;
m is an integer equal to 0, 1, 2, or 3;
n is an integer equal to 0, 1, 2, or 3;
$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or SO$_2$—$R^K$;
$R^8$ is H, $C_{1-6}$ alkyl, $C_{1-6}$ haloalkyl or $C_{3-6}$ cycloalkyl;
$R^K$ is:

(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) $C_{1-6}$ alkyl substituted with C(O)O—$C_{1-6}$ alkyl,
(9) $C_{1-6}$ alkyl substituted with C(O)OH,
(10) $C_{1-6}$ alkyl substituted with C(O)—$C_{1-6}$ alkyl,
(11) N(H)—$C_{1-6}$ alkyl,
(12) N(—$C_{1-6}$ alkyl)$_2$,
(13) $C_{1-6}$ alkyl substituted with NH$_2$, N(H)—$C_{1-6}$ alkyl, or N(—$C_{1-6}$ alkyl)$_2$,
(14) AryA,
(15) $C_{1-6}$ alkyl substituted with AryA,
(16) O—$C_{1-6}$ alkyl substituted with AryA,
(17) HetA,
(18) $C_{1-6}$ alkyl substituted with HetA,
(19) O—$C_{1-6}$ alkyl substituted with HetA,

(20) HetB,
(21) O-HetB, or
(22) O—$C_{1-6}$ alkyl substituted with HetB;

each AryA is an aryl which is independently phenyl or naphthyl, wherein the phenyl or naphthyl is optionally substituted with from 1 to 3 $Y^B$;

each HetA is a heteroaryl which is independently (i) a 5- or 6-membered monocyclic heteroaromatic ring containing from 1 to 4 heteroatoms independently selected from N, O and S, or (ii) is a 9-, 10- or 11-membered bicyclic heteroaromatic ring containing from 1 to 6 heteroatoms independently selected from N, O and S; wherein the monocyclic ring (i) or the bicyclic ring (ii) is optionally substituted with from 1 to 3 $Y^C$; and each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with from 1 to 3 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)NH$_2$, C(O)N(H)—$C_{1-6}$ alkyl, C(O)N(—$C_{1-6}$ alkyl)$_2$, C(O)H, C(O)—$C_{1-6}$ alkyl, CO$_2$H, CO$_2$—$C_{1-6}$ alkyl, SO$_2$H, or SO$_2$—$C_{1-6}$ alkyl.

2. The compound according to claim 1, or a pharmaceutically acceptable salt thereof, wherein $R^6$ is:

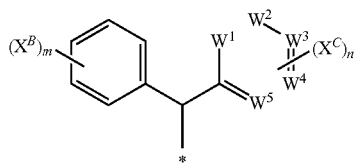

wherein $W^1$ to $W^5$ are independently CH or N, with the proviso that no more than three are N, and $R^{6A}$ is H.

3. The compound according to claim 2, or a pharmaceutically acceptable salt thereof, wherein $Z^1$ is $C_{1-6}$alkyl and $Z^2$ is

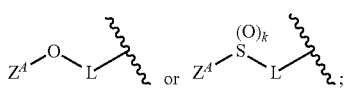

and L is —CH$_2$—.

4. The compound according to claim 3, or a pharmaceutically acceptable salt thereof, wherein $Z^1$ is methyl.

5. The compound according to claim 2, or a pharmaceutically acceptable salt thereof, wherein $Z^1$ is

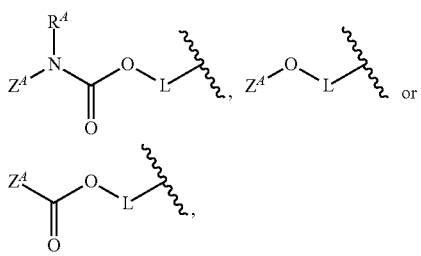

and $Z^2$ is

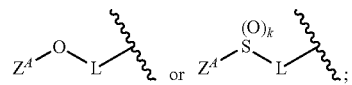

wherein L is —CH$_2$—.

6. The compound according to claim 2, or a pharmaceutically acceptable salt thereof, wherein $Z^2$ is $C_{1-6}$alkyl and $Z^1$ is

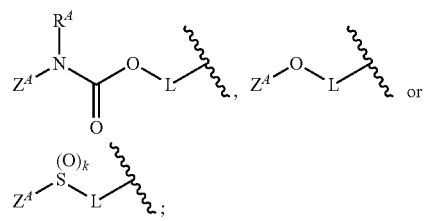

and L is —CH$_2$—.

7. The compound according to claim 6, or a pharmaceutically acceptable salt thereof, wherein $Z^2$ is methyl.

8. The compound according to claim 7, or a pharmaceutically acceptable salt thereof, wherein $Z^1$ is

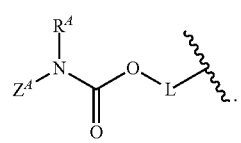

9. The compound according to claim 1 of Formula Ia

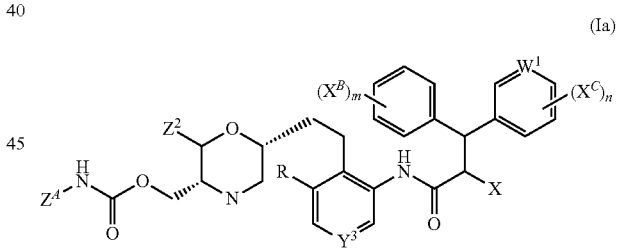

(Ia)

or a pharmaceutically acceptable salt thereof, wherein $W^1$ is CH or N.

10. The compound according to claim 9, or a pharmaceutically acceptable salt thereof, wherein:
$Z^2$ is methyl
R is H or fluoro,
$Y^3$ is CH or N,
$X^B$ and $X^C$ are independently selected from F, Cl, Br, —OCH$_3$, —CF$_3$ and —OCF$_3$, and m and n are independently 0, 1 or 2.

11. The compound according to claim 10, or a pharmaceutically acceptable salt thereof, wherein X is selected from: H, —NH$_2$ and —N(H)—C(O)—$R^K$ wherein $R^K$ is O—$C_{1-6}$ alkyl or O—$C_{1-6}$ fluoroalkyl.

12. The compound according to claim 11, or a pharmaceutically acceptable salt thereof, wherein $W^1$ is CH, one $X^B$ group is present and substituted at the 4-position, one or two $X^C$ groups are present and substituted at the 3- or 3,5-positions respectively, and the $X^B$ group is a different group with respect to either $X^C$ group.

13. The compound according to claim 10, or a pharmaceutically acceptable salt thereof, wherein $Z^A$ is selected from the group consisting of:
   (1) hydrogen,
   (2) $C_{1-10}$ alkyl,
   (3) $C_{2-10}$ alkenyl, and
   (4) $C_{3-7}$ cycloalkyl,
wherein said $C_{1-10}$ alkyl, $C_{2-10}$ alkenyl and $C_{3-7}$ cycloalky are optionally substituted with 1 to 6 substituents as allowed by valence independently selected from the group consisting of: fluoro, hydroxy, carbamoyl, $C_{3-6}$ cycloalkyl, C(O)O—$C_{1-6}$ alkyl, C(O)OH, C(O)—$C_{1-6}$ alkyl, N(H)—$C_{1-6}$ alkyl, N(—$C_{1-6}$ alkyl)$_2$, ArylA, HetA and HetB.

14. The compound according to claim 13, or a pharmaceutically acceptable salt thereof, wherein $Z^A$ is $C_{1-10}$ alkyl, optionally substituted with 1 to 6 substituents as allowed by valence independently selected from the group consisting of: fluoro and hydroxy.

15. The compound according to claim 14, or a pharmaceutically acceptable salt thereof, wherein $Z^A$ is —(CH$_2$)$_{0-4}$—CF$_3$.

16. A compound selected from the group consisting of:
   N-(2-{2-[(2R,5R,6S)-6-{[(4-chlorophenyl)sulfanyl]methyl}-5-methylmorpholin-2-yl]ethyl}phenyl)-Nα-(methoxycarbonyl)-β-phenyl-L-phenylalaninamide;
   N-(2-{2-[(2R,5R,6S)-6-{[(4-cyanophenyl)sulfanyl]methyl}-5-methylmorpholin-2-yl]ethyl}phenyl)-Nα-(methoxycarbonyl)-β-phenyl-L-phenylalaninamide;
   N-(2-{2-[(2R,5R,6S)-6-{[(3-chloropyridin-2-yl)sulfanyl]methyl}-5-methylmorpholin-2-yl]ethyl}phenyl)-Nα-(methoxycarbonyl)-β-phenyl-L-phenylalaninamide;
   methyl [(2S)-1-{[2-(2-{(2R,5R,6S)-5-methyl-6-[(quinolin-5-ylsulfanyl)methyl]morpholin-2-yl}ethyl)phenyl]amino}-1-oxo-3,3-diphenylpropan-2-yl]carbamate;
   methyl N-[(1S)-1-benzhydryl-2-[[2[2-[(2R,5R,6S)-5-methyl-6-[[5-(4-pyridyl)-1,3,4-oxadiazol-2-yl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-[[5-[(5-methylpyrazol-1-yl)methyl]-1,3,4-oxadiazol-2-yl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-[[5-[(2-methylthiazol-4-yl)methyl]-1,3,4-oxadiazol-2-yl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-6-[(5-chloro-2-pyridyl)sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-(quinoxalin-2-ylsulfanylmethyl)morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-(1H-pyrazolo[3,4-d]pyrimidin-4-ylsulfanylmethyl)morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-[(1-methylpyrazolo[3,4-d]pyrimidin-4-yl)sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-6-[(3,4-dimethylphenyl)sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-(1,3,4-thiadiazol-2-ylsulfanylmethyl)morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-[[2-(trifluoromethyl)quinazolin-4-yl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-6-[[5-[1-hydroxy-1-(trifluoromethyl)propyl]thiazol-2-yl]sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-6-[(4,5-dimethyloxazol-2-yl)sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-6-[[5-(difluoromethoxy)-1H-benzimidazol-2-yl]sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6 S)-5-methyl-6-[[4-methyl-6-(trifluoromethyl)pyrimidin-2-yl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-(4-pyridyl sulfanylmethyl)morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-[[3-(trifluoromethyl)-2-pyridyl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-6-[(5-chlorothiazolo[5,4-b]pyridin-2-yl)sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-6-(1H-imidazo[4,5-b]pyridin-2-ylsulfanylmethyl)-5-methyl-morpholin-2-yl]ethyl]phenyl]amino]-2-oxo-ethyl]carbamate;
   methyl N-[(1S)-1-benzhydryl-2-[[2[2-[(2R,5R,6S)-6-[[9-[(2R,3R,4S,5R)-3,4-dihydroxy-5-(hydroxymethyl)tetrahydrofuran-2-yl]purin-6-yl]sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-5-methyl-6-(1H-1,2,4-triazol-3-ylsulfanylmethyl)morpholin-2-yl]ethyl]phenyl]amino]-2-oxo-ethyl]carbamate;
   methyl N-[(1S)-1-[[2-[2-[(2R,5R,6S)-6-[(4-amino-1H-pyrazolo[3,4-d]pyrimidin-6-yl)sulfanylmethyl]-5-methyl-morpholin-2-yl]ethyl]phenyl]carbamoyl]-2,2-diphenyl-ethyl]carbamate;
   methyl N-[(1S)-1-benzhydryl-2-[[2[2-[(2R,5R,6S)-5-methyl-6-[[5-(pyrrolidin-1-ylmethyl)-1,3,4-oxadiazol-2-yl]sulfanylmethyl]morpholin-2-yl]ethyl]phenyl]amino]-2-oxo-ethyl]carbamate;
   methyl N-[(1S)-1-benzhydryl-2-[[2[2-[(2R,5R,6S)-6-[(3-cyano-4,6-dimethyl-2-pyridyl)sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-6-[[1-(2-dimethylaminoethyl)tetrazol-5-yl]sulfanylmethyl]-5-methyl-morpholin-2-yl]ethyl]phenyl]amino]-2-oxo-ethyl]carbamate;
   methyl N-[(1S)-1-benzhydryl-2-[[2[2-[(2R,5R,6S)-6-(1H-imidazol-2-ylsulfanylmethyl)-5-methyl-morpholin-2-yl]ethyl]phenyl]amino]-2-oxo-ethyl]carbamate;

[(2S,3R,6R)-6-[2-(2-{[N-(methoxycarbonyl)-β-phenyl-L-phenylalanyl]amino phenyl)ethyl]-2-({[5-(pyridin-4-yl)-1,3,4-oxadiazol-2-yl]sulfanyl}methyl)morpholin-3-yl]methyl acetate;

N-(2-{2-[(2R,5R,6S)-5-(hydroxymethyl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide;

N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide;

N-(2-{2-[(2R,5R,6S)-5-(1H-imidazol-2-yl)-6-({[5-(pyridin-4-yl)-1,3,4-oxadiazol-2-yl]sulfanyl}methyl)morpholin-2-yl]ethyl}phenyl)-Nα-(methoxycarbonyl)-β-phenyl-L-phenylalaninamide;

Nα-(methoxycarbonyl)-β-phenyl-N-(2-{2-[(2R,5R,6S)-6-({[5-(pyridin-4-yl)-1,3,4-oxadiazol-2-yl]sulfanyl methyl)-5-({[(2,2,2-trifluoroethyl)carbamoyl]oxy methyl)morpholin-2-yl]ethyl}phenyl)-L-phenylalaninamide;

N-(2-{2-[(2R,5R,6S)-5-({[(4-fluorobenzyl)carbamoyl]oxy}methyl)-6-({[5-(pyridin-4-yl)-1,3,4-oxadiazol-2-yl]sulfanyl}methyl)morpholin-2-yl]ethyl phenyl)-Nα-(methoxycarbonyl)-β-phenyl-L-phenylalaninamide;

N-[2-(2-{(2R,5R,6S)-5-[(carbamoyloxy)methyl]-6-methylmorpholin-2-yl}ethyl)-3-fluorophenyl]-4-fluoro-β-(4-fluorophenyl)-L-phenylalaninamide;

4-fluoro-N-[3-fluoro-2-(2-{(2R,5R,6S)-6-methyl-5-[({[(1S)-2,2,2-trifluoro-1-methylethyl]carbamoyl}oxy)methyl]morpholin-2-yl ethyl)phenyl]-β-(4-fluorophenyl)-L-phenylalaninamide;

4-fluoro-N-[3-fluoro-2-(2-{(2R,5R,6S)-5-[({[(1R)-1-(4-fluorophenyl)propyl]carbamoyl oxy)methyl]-6-methylmorpholin-2-yl}ethyl)phenyl]-β-(4-fluorophenyl)-L-phenylalaninamide;

Nα-(methoxycarbonyl)-N-(2-{2-[(2R,5R,6S)-5-methyl-6-({[6-(4-methylpiperazin-1-yl)pyrimidin-4-yl]sulfanyl}methyl)morpholin-2-yl]ethyl}phenyl)-β-phenyl-L-phenylalaninamide;

N-(2-{2-[(2R,5R,6 S)-6-{[(4-chlorophenyl)sulfonyl]methyl}-5-methylmorpholin-2-yl]ethyl}phenyl)-Nα-(methoxycarbonyl)-β-phenyl-L-phenylalaninamide;

N-(2-{2-[(2R,5R,6S)-6-{[(R)-(4-chlorophenyl)sulfonyl]methyl-5-methylmorpholin-2-yl]ethyl}phenyl)-Nα-(methoxycarbonyl)-β-phenyl-L-phenylalaninamide;

N-(2-{2-[(2R,5R,6 S)-5-[(benzyloxy)methyl]-6-(hydroxymethyl)morpholin-2-yl]ethyl}phenyl)-Nα-(methoxycarbonyl)-β-phenyl-L-phenylalaninamide;

Nα-(methoxycarbonyl)-β-phenyl-N-(2-{2-[(2R,5R,6S)-6-{[(5-pyridin-4-yl-1,3,4-oxadiazol-2-yl)sulfanyl]methyl}-5-({[(2,2,2-trifluoroethyl)carbamoyl]oxy}methyl)morpholin-2-yl]ethyl}phenyl)-L-phenylalaninamide;

N-(2-{2-[(2R,5R,6S)-6-{[(4-chlorobenzyl)oxy]methyl-5-({[(2,2,2-trifluoroethyl)carbamoyl]oxy}methyl)morpholin-2-yl]ethyl phenyl)-Nα-(methoxycarbonyl)-β-phenyl-L-phenylalaninamide;

4-fluoro-N-(5-fluoro-4-{2-[(2R,5R,6R)-6-methyl-5-({[(2,2,2-trifluoroethyl)carbamoyl]oxy}methyl)morpholin-2-yl]ethyl pyridin-3-yl)-β-(4-fluorophenyl)-L-phenylalaninamide;

N-(2-{2-[(2R,5R,6S)-6-(hydroxymethyl)-5-({[(2,2,2-trifluoroethyl)carbamoyl]oxy methyl)morpholin-2-yl]ethyl}phenyl)-Nα-(methoxycarbonyl)-β-phenyl-L-phenylalaninamide;

4-fluoro-N-(3-fluoro-2-{2-[(2R,5R,6R)-6-methyl-5-({[(2,2,2-trifluoroethyl)carbamoyl]oxy}methyl)morpholin-2-yl]ethyl}phenyl)-β-(4-fluorophenyl)-L-phenylalaninamide;

4-fluoro-N-(3-fluoro-2-2-[(2R,5R,6R)-5-({[(4-fluorobenzyl)carbamoyl]oxy}methyl)-6-methylmorpholin-2-yl]ethyl}phenyl)-β-(4-fluorophenyl)-L-phenylalaninamide;

4-fluoro-N-(3-fluoro-2-{2-[(2R,5R,6S)-5-(hydroxymethyl)-6-methylmorpholin-2-yl]ethyl}phenyl)-β-(4-fluorophenyl)-L-phenylalaninamide;

4-fluoro-N-(3-fluoro-2-{2-[(2R,5R,6S)-6-methyl-5-({[(2,2,2-trifluoroethyl)carbamoyl]oxy}methyl)morpholin-2-yl]ethyl}phenyl)-β-(4-fluorophenyl)-L-phenylalaninamide;

4-fluoro-N-(5-fluoro-4-{[(2S,5R,6R)-6-methyl-5-({[(2,2,2-trifluoroethyl)carbamoyl]oxy}methyl)morpholin-2-yl]methoxy}pyridin-3-yl)-β-(4-fluorophenyl)-L-phenylalaninamide;

N-[4-({(2S,5R,6R)-5-[(carbamoyloxy)methyl]-6-methylmorpholin-2-yl}methoxy)-5-fluoropyridin-3-yl]-4-fluoro-β-(4-fluorophenyl)-L-phenylalaninamide;

N-[4-(2-{(2R,5R,6S)-5-[(carbamoyloxy)methyl]-6-methylmorpholin-2-yl}ethyl)-5-fluoropyridin-3-yl]-4-fluoro-β-(4-fluorophenyl)-L-phenylalaninamide;

4-fluoro-N-(5-fluoro-4-{2-[(2R,5R,6S)-6-methyl-5-({[(2,2,2-trifluoroethyl)carbamoyl]oxy}methyl)morpholin-2-yl]ethyl}pyridin-3-yl)-β-(4-fluorophenyl)-L-phenylalaninamide;

4-fluoro-N-(3-fluoro-2-{2-[(2R,5R,6R)-6-methyl-5-({[(2,2,2-trifluoroethyl)carbamoyl]oxy}methyl)morpholin-2-yl]ethyl}phenyl)-β-(4-fluorophenyl)-L-phenylalaninamide;

4-fluoro-N-(3-fluoro-2-{2-[(2R,5R,6R)-5-({[(4-fluorobenzyl)carbamoyl]oxy}methyl)-6-methylmorpholin-2-yl]ethyl}phenyl)-β-(4-fluorophenyl)-L-phenylalaninamide;

4-fluoro-N-(5-fluoro-4-{2-[(2R,5R,6R)-6-methyl-5-({[(2,2,2-trifluoroethyl)carbamoyl]oxy}methyl)morpholin-2-yl]ethyl}pyridin-3-yl)-β-(4-fluorophenyl)-L-phenylalaninamide;

4-fluoro-N-[3-fluoro-2-(2-{(2R,5R,6S)-5-[({[(1R)-1-(4-fluorophenyl)-2-methylpropyl]carbamoyl}oxy)methyl]-6-methylmorpholin-2-yl}ethyl)phenyl]-β-(4-fluorophenyl)-L-phenylalaninamide;

N-[2-(2-(2R,5R,6 S)-5-[({[(R)-cyclopropyl(4-fluorophenyl)methyl]carbamoyl oxy)methyl]-6-methylmorpholin-2-yl}ethyl)-3-fluorophenyl]-4-fluoro-β-(4-fluorophenyl)-L-phenylalaninamide;

N-{3-fluoro-2-[(2S,4aR,9aS)-2,3,4,4a,9,9a-hexahydroindeno[2,1-b][1,4]oxazin-2-ylmethoxy]phenyl}-β-phenyl-L-phenylalaninamide;

4-fluoro-N-[3-fluoro-2-(2-{(2R,5R,6S)-6-methyl-5-[({[(1R)-2,2,2-trifluoro-1-methylethyl]carbamoyl}oxy)methyl]morpholin-2-yl}ethyl)phenyl]-β-(4-fluorophenyl)-L-phenylalaninamide;

[(2S,3R,6R)-6-[2-(2-{[3,3-bis(4-fluorophenyl)propanoyl]amino}-6-fluorophenyl)ethyl]-3-(hydroxymethyl)morpholin-2-yl]methyl (2,2,2-trifluoroethyl)carbamate;

4-fluoro-N-(3-fluoro-2-{2-[(2R,5R,6S)-5-(hydroxymethyl)-6-({[(2,2,2-trifluoroethyl)carbamoyl]oxy}methyl)morpholin-2-yl]ethyl}phenyl)-β-(4-fluorophenyl)-L-phenylalaninamide; and N-(2-{2-[(2R,5R,6 S)-6-[(4-cyanophenoxy)methyl]-5-({[(2,2,2-trifluoroethyl)carbamoyl]oxy}methyl)morpholin-2-yl]ethyl}phenyl)-Nα-(methoxycarbonyl)-β-phenyl-L-phenylalaninamide;

and pharmaceutically acceptable salts thereof.

17. A pharmaceutical composition comprising an effective amount of a compound according to claim 1 or a pharmaceutically acceptable salt thereof, and a pharmaceutically acceptable carrier.

18. A method for the treatment of infection by HIV or for the treatment, prophylaxis or delay in the onset of AIDS in a subject in need thereof, which comprises administering to the subject an effective amount of the compound according claim 1 or a pharmaceutically acceptable salt thereof.

19. A pharmaceutical composition comprising an effective amount of a compound according to claim 1, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents.

20. The pharmaceutical composition of claim 19, wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

\* \* \* \* \*